United States Patent [19]
Ochoa et al.

[11] Patent Number: 5,725,855
[45] Date of Patent: Mar. 10, 1998

[54] METHOD OF TREATING TUMORS WITH CD8+-DEPLETED OR CD4+ T CELL SUBPOPULATIONS

[75] Inventors: Augusto Carlos Ochoa; Mark L. Saxton, both of Frederick; Dan L. Longo, Kensington, all of Md.

[73] Assignees: The United States of America as represented by the Department of Health and Human Services, Washington, D.C.; Regents of the Univ. of Minnesota, Minneapolis, Minn.

[21] Appl. No.: 215,767

[22] Filed: Mar. 22, 1994

Related U.S. Application Data

[63] Continuation-in-part of Ser. No. 960,297, Oct. 13, 1992, abandoned, which is a continuation of Ser. No. 681,074, Apr. 5, 1991, abandoned.

[51] Int. Cl.$^6$ .................. A61K 35/12; A61K 35/14; A61K 35/26; A61K 35/28
[52] U.S. Cl. ........................ 424/93.71; 424/93.7
[58] Field of Search ............. 435/240.2, 240.25, 435/2, 240.21, 325, 363, 366, 372, 372.3, 383, 385, 386; 424/93.7, 93.71

[56] References Cited

U.S. PATENT DOCUMENTS

| | | |
|---|---|---|
| 4,690,915 | 9/1987 | Rosenberg ................ 514/2 |
| 4,808,151 | 2/1989 | Dunn et al. . |

FOREIGN PATENT DOCUMENTS

| | | |
|---|---|---|
| 0 405 972 | 1/1991 | European Pat. Off. . |
| 0 409 655 | 1/1991 | European Pat. Off. . |
| WO 88/00970 | 2/1988 | WIPO . |
| WO 89/05657 | 6/1989 | WIPO . |
| WO 89/09831 | 10/1989 | WIPO . |
| WO 90/04633 | 5/1990 | WIPO . |

OTHER PUBLICATIONS

P.M. Anderson et al., Cancer Immunol. Immunother., 1988, 27, 82, "Augmentation of cell number and LAK activity in peripheral blood mononuclear cells activated with anti-CD3 and interleukin-2".
P.M. Anderson et al., J. Immunol., 1989, 142, 1383, "Anti-CD3 + IL-2 Stimulated Murine Killer Cells in Vitro Generation and in Vivo Antitumor Activity".
L.S. Davis et al., Cell Immunol., 1989, 118, 208, "T Cell Activation Induced by Anti-CD3 Antibodies Requires Prolonged Stimulation of Protein Kinase C".
Dianzani et al., Eur. J. Immunol., 19: 1037 (1989). "CD8+ CD11b+ peripheral blood T lymphocytes contain lymphokine-activated killer cell precursors".
Geller et al., J. Immunol., 146(10): 3280 (1991). "Generation of Lymphokine–Activated Killer Activity in T Cells".
T.D. Geppert et al., J. Clin. Invest., 1988, 81, 1497, "Activation of T Lymphocytes by Immobilized Monoclonal Antibodies to CD3".

E.A. Grimm et al., J. Exp. Med., 1982, 155, 1823, "Lymphokine–Activated Killer Cell Phenomenon".
M. Izquierdo et al., Clin. Exp. Immunol., 1988, 74, 300, "Selective T cell subset depletion with anti–CD4 and anti–CD8 intact ricin immunotoxins".
C.M. Loeffler et al., Cancer Res., 51: 2127 (1991). "Antitumor Effects of Interleukin 2 Liposomes and Anti–CD3–Stimulated T–Cells Against Murine MCA–38 Hepatic Metastasis".
E. Lotzova et al., Nat. Immun. Cell Growth Regul., 1987, 6, 219, "Augmentation of Antileukemia Lytic Activity by OKT3 Monoclonal Antibody: Synergism of OKT3 and Interleukin–2".
A.C. Ochoa et al., Cancer Res., 49: 963 (1989). "Lymphokine–activated Killer Activity in Long–Term Cultures with Anti–CD3 plus Interleukin 2: Identification and Isolation of Effector Subsets".
A.C. Ochoa et al., J. Immunol., 1987, 138, 2728, "Long-Term Growth of Lymphokine–Activated Killer (LAK) Cells: Role of Anti–CD3, β–IL 1, Interferon–γ and –β".
L.E. Samuelson et al., Proc. Natl. Acad. Sci. USA, 87: 4358 (1990). "Association of the fyn protein–tyrosine kinase with the T–cell antigen receptor".
R. Schwab et al., J. Immunol., 1985, 135, 1714. "Requirements for T–Cell Activation by OKT3 Monoclonal Antibody: Role of Modulation of T3 Molecules and Interleukin".
S. Shu et al., J. Immunol., 1985, 135, 2895, "Adoptive Immunotherapy of a Newly Induced Sarcoma: Immunologic Characteristics of Effector Cells".
Smyth, J. Exp. Med., 171: 1269 (1990). "Interleukin 2 Induction of Pore–Forming Protein Gene Expression in Human Peripheral Blood CD8+ T Cells".

(List continued on next page.)

Primary Examiner—Lila Feisee
Assistant Examiner—Phillip Gambel
Attorney, Agent, or Firm—Foley & Lardner

[57] ABSTRACT

The present invention provides a method for enhancing the immunotherapeutic activity, e.g., antitumor activity, of immune cells by depleting immune cells of a cell subset that down-regulates the immune response, such as either CD4+ or CD8+ lymphocytes. The remaining depleted immune cell population or the separated immune cell subsets then are cultured in the presence of an antibody to a lymphocyte surface receptor, preferably an anti-CD3 monoclonal antibody (MoAb), optionally in the presence of a relatively minor amount of interleukin-2 (IL-2). These stimulated cells then are optionally additionally cultured in the presence of IL-2 without an antibody to a lymphocyte surface receptor. The present invention also provides a method of treating a mammal having tumors or immunizing a mammal against tumors by administering the stimulated depleted immune cell population or a stimulated immune cell subset to a mammal, advantageously together with an immunosuppressant, and with liposomal IL-2. The invention further provides a method of transferring the immunity of mammals that are treated or immunized in accordance with the invention by extracting splenocytes from these mammals and administering these splenocytes to a second mammal.

4 Claims, 5 Drawing Sheets

OTHER PUBLICATIONS

Smyth, J. Immunol., 146: 3289 (1991), "Regulation of Lymphokine–Activated Killer Activity and Pore–forming Protein Gene Expression in Huan Peripheral Blood CD8$^+$ T Lymphocytes".

C.–C. Ting et al., Immunol. Invest., 1990, 19, 347, "Anti–CD3 Antibody–Induced Activated Killer Cells Subsets of Killer Cells that Mediate Fast or Slow Lytic Reactions".

M. C. Turco et al., Blood, 1989, 74, 1651, "Proliferative Pathways in CD1$^-$CD3$^+$ CD4$^{++}$ CD8$^+$ T Prolymphocytic Leukemic Cells: Analysis with Monoclonal Antibodies and Cytokines".

R. J. van de Griend et al., J. Immunol., 1987, 138, 1627, "Lysis of Tumor Cells by CD3$^+$ 4$^-$8$^-$16$^+$ T Cell Receptor $\alpha\beta$– Clones, Regulated Via CD3 and CD16 Activation Sites, Recombinant Interleukin 2, and Interferon $\beta$".

W. H. West et al., J. Immunol., 1977, 118, 355, "Natural Cytotoxic Reactivity of Human Lymphocytes Against a Myeloid Cell Line: Characterization of Effector Cells".

Ochoa et al., FASEB Journal, 3(3)A: 826 (abstract) (1989), "T Cels Can Develop High Lak Activity: Possible Regulatory Circuits".

Lotze et al., Cancer Res., 41: 4420 (1981), "Lysis of Fresh and Cultured Autologous Tumor by Human Lymphocytes Cultured in T–Cell Growth Factor".

Belldegrun et al., Cancer Res., 48: 206 (1988), "Interleukin 2 Expanded Tumor–infiltrating Lymphocytes in Human Renal Cell Cancer: Isolation, Characterization, and Antitumor Activity".

Maghazachi et al., J. Immunol., 141: 4039 (1988), "Influence of T Cells on the Expression of Lymphokine–Activated Killer Cell Activity and In Vivo Tissue Distribution".

Damle et al., J. Exp. Med., 158: 159 (1983), "Immunoregulatory T Cell Circuits in Man".

Lewis et al., PNAS, USA, 85: 9743 (1988), "Restricted production of interleukin 4 by activated human T cells".

Halvorsen et al., Scand J. Immunol. 27, 555–563, 1988, "Role of Accessory Cells in the Activation of Pure T Cells via the T Cell Receptor–CD3 Complex or with Phytohaemagglutinin".

Halvorsen et al., Scand J. Immunol. 26, 197–205, 1987, "Activation of Resting, Pure CD4$^+$, and CD8$^+$ Cells via CD3".

Tsoukas et al. "Activation of Resting T Lymphocytes By Anti–CD3 (T3) Antibodies in the Absence of Monocytes", The Journal of Immunology, vol. 135, No. 3, Sep. 1985, pp. 1719–1723.

Hogan et al., "Lymphokine–Activated and Natural Killer Cell Activity in Human Intestinal Mucosa", The Journal of Immunology, vol. 135, No. 3, Sep. 1985, pp. 1731–1738.

Smyth, et al. Journal of Experimental Medicine, vol. 171, pp. 1269–1281; Apr. 1990.

Anderson, et al., Anti–CD3 + IL–2 Stimulated Murine Killer Cells: In Vitro Generation and In Vivo Antitumor Activity. J. Immunol. vol. 142, No. 4, 1383–1394, 1989.

Lotze, M.T., Transplantation and Adoptive Cellular Therapy of Cancer: The Role of T– Cell Growth Factors. Cell Transplant. vol. 2, pp. 33–47, 1993.

Lindeman et al., Lymphokine Activated Killer Cells, Blut vol. 59, pp. 375–384, 1989.

Osband et al., Problems in the Investigational Study and Clinical Use of Cancer Immunotherapy, Immunol. Today, vol. 11, No. 6, 1990.

L Whiteside et al. Cancer Immunol. Immunother. 39:15–21 (1994).

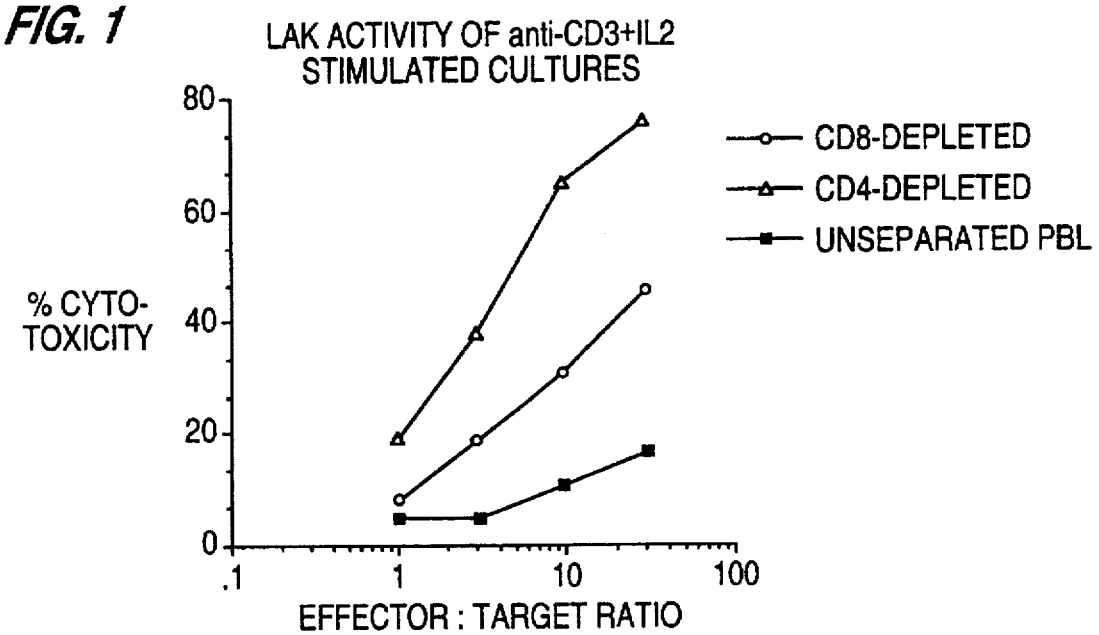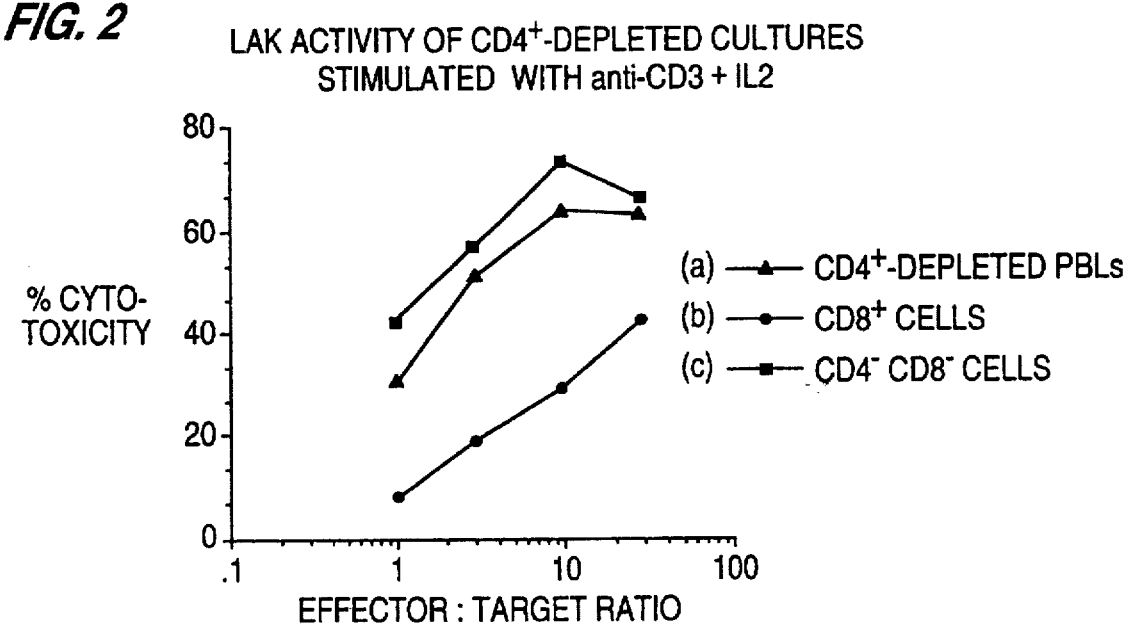

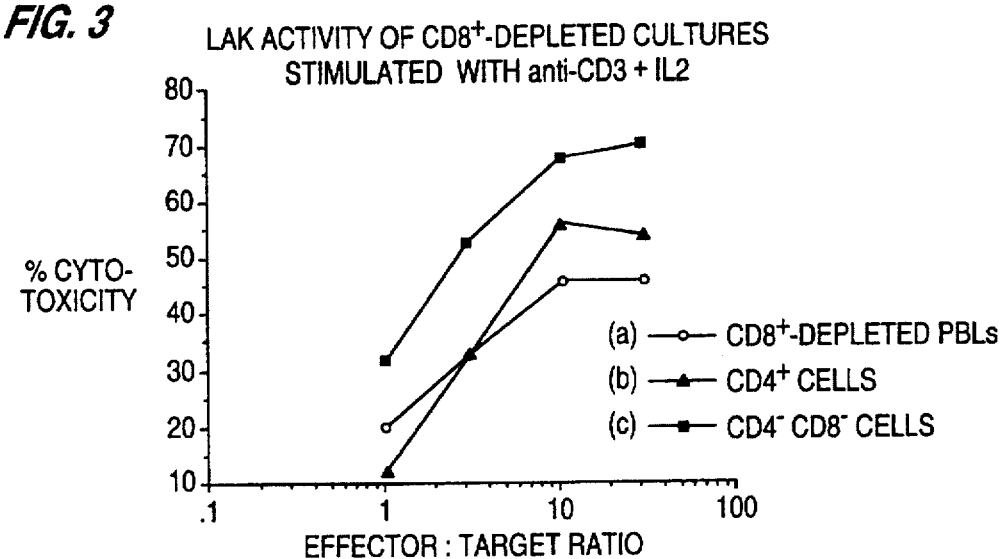
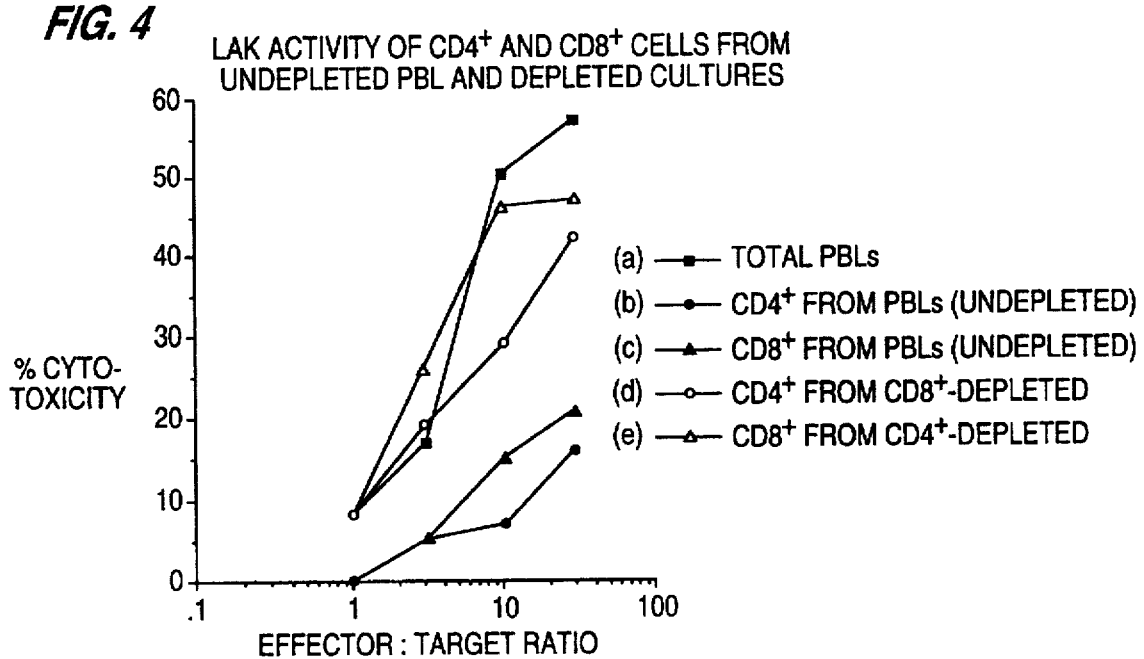

METHOD OF TREATING TUMORS WITH CD8⁺-DEPLETED OR CD4⁺ T CELL SUBPOPULATIONS

This application is a continuation-in-part of Ser. No. 07/960,297 filed Oct. 13, 1992, now abandoned, which is a continuation of application Ser. No. 07/681,074 filed Apr. 5, 1991, now abandoned.

FIELD OF THE INVENTION

This invention relates to enhancing the immunotherapeutic activity of immune cells. Specifically, this invention relates to the stimulation of antitumor activity of immune cells upon the depletion or positive selection of specific cells or cell subsets of T lymphocytes, and the use of stimulated depleted or positively selected cells or cell subsets of T lymphocytes in reducing tumor volume in mammals, and in immunizing mammals against tumors. This invention also relates to the use of stimulated depleted or positively selected cells or cell subsets of T lymphocytes in increasing the production of colony forming units.

BACKGROUND OF THE INVENTION

Peripheral blood mononuclear lymphocytes (PBLs) can be stimulated to develop lytic activity against fresh tumor cells, as well as several natural killer (NK) resistant targets, such as Daudi and HL60, after relatively short-term (3–5 days) culturing in the presence of recombinant interleukin-2 (IL-2). See, for example, M. Lotze et al., Cancer Res., 41, 4420 (1981); C. Grimm et al., J. Exp. Med., 155, 1823 (1982); and E. A. Grimm et al., "The Lymphokine-Activated Killer Cell Phenomenon: In Vitro and In Vivo Studies," in INTERLEUKINS, LYMPHOKINES AND CYTOKINES, S. Cohen and I. Oppenheim, eds., Academic Press, New York, p. 739 (1983). This function has been termed lymphokine activated killer (LAK) activity.

Initial reports suggested that precursors of cells with LAK activity did not express the T cell receptor as determined by anti-CD3 binding. See, E. A. Grimm et al., J. Exp. Meal., 157, 884 (1983). More recent reports have demonstrated that effector cells obtained from short-term culturing with IL-2 (2–5 days) are a CD3⁻ population of cells that express the NK markers CD16 and/or CD56. The CD3⁺ cells from such cultures have low lytic activity against NK-resistant targets. Thus, the CD3⁻ population, with the NK markers CD16 and/or CD56, is responsible for the great majority of the LAK activity in PBL cultures. That is, CD3⁻ cells appear to be the classical NK effector cells. See, for example, J. R. Ortaldo et al., J. Exp. Med., 164, 1193 (1986); S. Ferrini et al., J. Immunol., 138, 1297 (1987); K. Itoh et al., J. Immunol., 136, 3910 (1986); and J. H. Phillips et al., J. Exp. Med., 164, 814 (1986).

Reversible induction of NK activity in cloned cytotoxic lymphocytes in response to IL-2 and interferon (IFN) has been reported. See, C. G. Brooks, NATURE, 305, 155 (1983). Furthermore, the generation of large numbers of cells with LAK activity using relatively long-term cultures (10–30 days) of PBLs stimulated with the anti-CD3 monoclonal antibody (MoAb) OKT3, in combination with IL-2 has been reported (CD3-LAK cells or T-AK cells). See, A. C. Ochoa et al., J. Immunol., 138, 2728 (1987). The effector cells in these long-term IL-2 and OKT3 cultures include CD3⁺ T cells, CD3⁻ cells, as well as a CD3⁺ population that is both CD4 and CD8 negative, and expresses the γδ chains of the T cell receptor. In contrast, the effector cells in short-term IL-2 and OKT3 cultures (2–5 days) are predominantly CD3⁻ cells.

Numerous studies have shown that very little LAK activity appears to be mediated by the classically described CD4⁺ or CD8⁺ T cells. Furthermore, CD4⁺ or CD8⁺ cells isolated from cultures of mixed PBL populations, which are activated with an antibody to a lymphocyte surface receptor, such as the anti-CD3 monoclonal antibody OKT3, and continuously cultured with IL-2, do not develop significant levels of NK or LAK activity, as determined immediately upon their isolation from the total population. See, for example, A. C. Ochoa et al., Cancer Res., 49, 963 (1989). For example, at an effector to target ratio of about 30:1, i.e., a ratio of the number of T cells capable of mediating cytotoxicity to the number of tumor cell line targets, the cytotoxicity of CD4⁺ or CD8⁺ subsets is no more than about 15–20%.

It has been noted that when PBLs are stimulated in mixed lymphocyte culture (MLC), the CD4⁺ cells are minimally cytotoxic. Furthermore, when the CD4⁺ population is stimulated in MLC in the absence of other T cells, they develop greater cytolytic activity. See, E. L. Reinherz et al., Proc. Natl. Acad. Sci. USA, 76, 4061 (1979). However, this cytotoxicity is antigen specific, and does not involve tumor killing activity.

It has also been recently shown that CD8⁺CD11b⁺ cells can develop LAK activity. In this specific situation, the CD8⁺ T cells were isolated from the PBL population before the initiation of culture in the presence of IL-2 alone. However, this method did not involve anti-CD3 MoAb stimulation; this method did involve separating the T cells with sheep red blood cells, which in itself can produce a stimulating signal through the CD2 receptor. Thus, NK cells, which express the CD2 receptor, can also be activated. See, U. Dianzani et al., Eur. J. Immunol., 19, 1037 (1989).

CD4⁺ and CD8⁺ cells cultured in the presence of IL-2 alone have been shown to express the lytic machinery, but LAK activity was not demonstrated nor was cell growth reported. See, M. J. Smyth et al., J. Exp. Med., 171, 1269 (1990). Finally, it has been shown that tumor infiltrating lymphocytes (TILs), which appear to be effective in the treatment of solid tumors, are primarily CD8⁺. See, for example, S. Shu et al., J. Immunol., 139, 295 (1987); and A. Belldegrun et al., Cancer Res., 48, 206 (1988).

The identification of cells that can mediate cytotoxicity, e.g., LAK activity, is important both for an understanding of the interactions of the immune system as well as for the potential development of effective methods of immunotherapy. One of the limitations of current LAK therapies for the treatment of tumors is that LAK cells appear to be transported via the reticuloendothelial system which, in some cases, limits the accessibility of LAK cells to certain tumors. See, for example, A. A. Maghazachi et al., J. Immunol., 141, 4039 (1988). T cells, on the other hand, circulate through the lymphatic system and provide greater accessibility to most tumors.

While most NK and LAK activity in cultures stimulated with IL-2 alone or IL-2+anti-CD3 appears not to be mediated by CD4⁺ or CD8⁺ cells, what has been needed is to determine if these T cells, under the appropriate conditions, could develop high cytotoxicity, e.g., specific or nonspecific lytic activity. Thus, what is needed is a method for the stimulation of immune cells to produce high cytotoxicity, preferably high nonspecific lytic, e.g. NK or LAK, activity in T cells, which can provide antitumor therapeutic efficacy.

Patients subjected to a bone marrow transplantation encounter a period of severe immune deficiency following high dose chemotherapy and/or total body irradiation (TBI)

since the patient's bone marrow is replaced with a small amount of healthy bone marrow cells that proliferates in the body until enough bone marrow cells have been generated to achieve a repopulation of the peripheral blood by red blood cells, platelets and white blood cells of the immune system. A typical bone marrow engraftment can take anywhere from 20 to 30 days to regenerate (engraft) sufficient quantities of bone marrow cells. During this period, the patient's immune system is virtually non-functional, and the patient must be closely monitored to prevent the onslaught of disease. These bone marrow cells can be induced to proliferate with factors such as G-CSF, GM-CSF, IL-3 and the like. However, all of these factors have to be administered at high doses that may be toxic to the patient. Thus, there exists a need to provide a method that is capable of stimulating the proliferation of bone marrow cells to increase the number of bone marrow cells produced and thereby decrease the time needed to regenerate a sufficient quantity of bone marrow cells.

There also exists a need to develop a method for reducing the tumor volume in mammals, and to generate long term immunity to tumor whereby an activated immune cell population that has the aforementioned high cytotoxicity, e.g. , NK or LAK activity, can be administered into the mammal to reduce the tumor volume. There also exists a need to develop a method for transferable immunity whereby immune cells of an immunized mammal are administered to another mammal of the same species, thereby conferring upon the other mammal an immunity to tumor.

SUMMARY OF THE INVENTION

It is an object of the present invention to develop a method for enhancing the immunotherapeutic activity of an immune cell population by the stimulation of the immune cells to produce high cytotoxicity, preferably high nonspecific lyric, e.g.; NK or LAK, activity in T cells, which can provide antitumor therapeutic efficacy. It also is an object of the invention to provide a method of treating a mammal having tumors using an immune cell population having an enhanced immunotherapeutic activity against these tumors.

It is an additional object of the present invention to provide a method for reducing the tumor volume in mammals, and to generate long term immunity to tumor. It also is an object of the invention to provide a method for transferable immunity whereby immune cells of an immunized mammal are administered to a second mammal, and the second mammal also develops an immunity to tumor.

In accordance with these and other objectives of the present invention, there is provided a method of enhancing the immunotherapeutic activity of immune cells by separating at least one mutually inhibiting cell subset within an immune cell population. By separating at least one mutually inhibiting cell subset within an immune cell population, the remaining immune cell population or the separated cell subset are capable of more fully expressing their immune function when stimulated. Stimulating the immune cells to enhance their immunotherapeutic activity can be effected primarily in one of four methods, the first two are "depletion methods" and the second two are "positive selection methods."

The first method includes: separating at least one cell subset, or subpopulation, that is capable of down-regulating the immunotherapeutic activity, e.g., cytotoxicity, of an immune cell population, from that immune cell population to form a "depleted immune cell populations"; and culturing the depleted immune cell population in the presence of an antibody to a lymphocyte surface receptor, optionally in the presence of IL-2, to form a "stimulated depleted immune cell population." In addition, the stimulated depleted immune cell population may optionally be further cultured in the presence of IL-2. Preferably, this method reduces or eliminates a regulatory mechanism from the immune cell population, which allows the remaining cells to more fully express their immune function. The immunotherapeutic activity of the remaining immune cell population, as represented by a measure of the ability of the immune cell population to reduce tumor volume, is increased when compared to a similarly treated undepleted immune cell population.

A second "depletion method" that enhances the immunotherapeutic activity in accordance with an object of the present invention, includes: (i) first culturing an immune cell population to form a "cultured immune cell population"; (ii) separating, i.e., a cell subset, or subpopulation, that is capable of developing immunotherapeutic activity, e.g., cytotoxicity to form a "stimulated depleted immune cell population"; and optionally (iii) separately culturing, i.e., subculturing, the stimulated depleted immune cell population in a second medium in the presence of IL-2. Preferably, by using this method and separating a cell subpopulation that is capable of down-regulating the immunotherapeutic activity of the cell population, the immunotherapeutic activity, as represented by the ability to reduce tumor volume, of this stimulated depleted immune cell population is enhanced when compared to a similarly treated undepleted cell population.

A third method ("positive selection method") of enhancing the immunotherapeutic activity in accordance with an object of the present invention, includes: separating and positively selecting at least one cell subset, or subpopulation, that is capable of up-regulating the immunotherapeutic activity, or developing the immunotherapeutic activity, of an immune cell population, from that immune cell population to form an "immune cell subset"; and then culturing the immune cell subset, e.g., CD4$^+$ or CD8$^+$ cells, in the presence of an antibody to a lymphocyte surface receptor, optionally in the presence of IL-2, to form a "stimulated immune cell subset." In addition, the stimulated depleted immune cell population may optionally be further cultured in the presence of IL-2. The immunotherapeutic activity of the stimulated immune cell subset, as represented by a measure of the ability of the immune cell population to reduce tumor volume, is increased when compared to a similarly treated undepleted immune cell population.

An additional positive selection method of enhancing the immunotherapeutic activity of an immune cell population in accordance with the present invention includes: (i) first culturing an immune cell population to form a "cultured immune cell populations"; (ii) separating, i.e., a cell subset, or subpopulation, that is capable of developing immunotherapeutic activity, e.g. , cytotoxicity to form a "stimulated immune cell subset"; and optionally (iii) separately culturing, i.e., subculturing, the stimulated immune cell subset population in a second medium in the presence of IL-2. Preferably, by using this method and separating a cell subpopulation that is capable of down-regulating the immunotherapeutic activity of the cell population, the immunotherapeutic activity, as represented by the ability to reduce tumor volume, of this immune cell subset is enhanced when compared to a similarly treated undepleted cell population. In addition, the separated cells preferably are CD4$^+$ or CD8$^+$ lymphocytes, or subsets of each of these populations.

In accordance with the methods described above, the depleted immune cell population, or advantageously, the immune cell subsets are preferably cultured in a first medium in the presence of an antibody to a lymphocyte surface receptor, optionally in the presence of IL-2. Also in accordance with the methods described above, the whole immune cell population preferably is cultured in a first medium in the presence of an antibody to a lymphocyte surface receptor, optionally in the presence of IL-2. More preferably, the cells (immune cell population or depleted cell population) are cultured in both IL-2 and an antibody to a lymphocyte surface receptor for only the first 48. hours. Thereafter, any culturing of either the stimulated depleted immune cell population or the stimulated immune cell subset preferably occurs in the presence of IL-2 without any additional amount of the antibody to a lymphocyte surface receptor for the purpose of preserving and growing the cells in vitro.

If the stimulated immune cell population or the stimulated immune cell subsets, i.e. "stimulated cells," are administered to a mammal shortly after the initial culturing, additional culturing in the presence of IL-2 is not necessary. IL-2 typically is administered to the mammal, however, in conjunction with the stimulated cells as a method of generating LAK activity in vivo. In addition, the depleted immune cell population, or advantageously, the immune cell subset, can be stimulated by an antibody to a lymphocyte surface receptor for the first 48 hours, and thereafter cultured with IL-2; however, further calturing with IL-2 is not necessary if the stimulated depleted immune cells are administered to a mammal shortly after culturing.

The stimulated depleted immune cell population or the stimulated immune cell subset can optionally be cultured in vitro in the presence of IL-2 to generate immune cells or immune cell subsets that exhibit increased immunotherapeutic activity. Subsequent in vitro culturing serves not only to proliferate and maintain the cell population, but to render the stimulated cells cytotoxic in vivo as well. The stimulated depleted immune cell population or the stimulated immune cell subset also can be injected in vivo after stimulation with the antibody against the surface receptor. These cells will then proliferate in vivo after I1–2 is administered. While not intending to be bound by any theory, it is believed that culturing the immune cell population or the immune cell subset in the presence of an antibody to a lymphokine surface receptor "primes" the cells to upregulate the production of IL-2 receptor sites on the cells. Thus, when IL-2 is further administered either in vivo in conjunction with the stimulated cells, or in vitro, the stimulated cells are more significantly stimulated by accepting more IL-2. These stimulated cells, when bound with IL-2, then are capable of lysing tumors because the IL-2 may generate a cascading signaling reaction within the cells to generate LAK activity.

Immune cell populations stimulated in accordance with any of the foregoing methods are useful in the following methods of treating mammals with tumors, immunizing mammals against tumors and transferring the immunity of the one mammal to another mammal.

In accordance with an additional object of the present invention there is provided a method of treating a mammal having tumors with immune cells having an enhanced immunotherapeutic activity, prepared by the procedures outlined above to prepare a stimulated depleted immune cell population or a stimulated immune cell subset; and then culturing the depleted immune cell population, or the cell subpopulation in the presence of an antibody to a lymphocyte surface receptor, optionally in the presence of IL-2. The stimulated depleted immune cell population or the stimulated immune cell subset then can optionally be cultured additionally in the presence of IL-2, although further culturing is not necessary. This method therefore includes (i) enhancing the immunotherapeutic activity of an immune cell population as described immediately above; (ii) administering the immune cell population into a mammal having tumors and optionally pretreated with an immunosuppressant; and (iii) administering IL-2, preferably liposomal IL-2, to the mammal in addition to the immune cell population of step (ii).

In accordance with another object of the present invention, there is provided a method of immunizing a mammal against tumor by (i) enhancing the immunotherapeutic activity of an immune cell population in accordance with any of the procedures outlined above; (ii) administering the stimulated depleted immune cell population or stimulated immune cell subset to a mammal having tumors, wherein the mammals are optionally pretreated with an immunosuppressant; and (iii) administering IL-2, preferably liposomal IL-2 to the mammal in addition to the stimulated depleted immune cell population or stimulated immune cell subset of step (ii).

In accordance with yet another object of the present invention, there is provided a method of transferring the immunity of one mammal to another mammal by (i) extracting and separating splenocytes from the spleen of a mammal immunized against tumors, whereby the mammal is immunized against tumors by (i) enhancing the immunotherapeutic activity of an immune cell population in accordance with any of the procedures outlined above; (ii) administering the stimulated depleted immune cell population or stimulated immune cell subset to a mammal, optionally pretreated with an immunosuppressant; and (iii) administering IL-2, preferably liposomal IL-2, to the mammal in addition to the stimulated depleted immune cell population or stimulated immune cell subset of step (ii) to produce an immunity in the mammal against tumors. Splenocytes of this treated mammal that has developed the aforementioned immunity then are extracted using conventional techniques and are administered to a second mammal, optionally with IL-2, preferably liposomal IL-2. The second mammal also is optionally pretreated with an immunosuppressant before administration of the splenocytes. In accordance with this method, the second mammal receiving the splenocytes also develops an immunity against tumors.

In accordance with yet another object of the present invention, there is provided a method of stimulating the proliferation of bone marrow cells comprising the steps of first enhancing the immunotherapeutic activity of an immune cell population in accordance with any of the procedures outlined above. The stimulated depleted immune cell population or stimulated immune cell subset can additionally be cultured in vitro with IL-2 for in vitro efficacy. These stimulated cells then are incubated in the presence of bone marrow, optionally in the presence of additional cytokines including granulocyte maerophage colony stimulating factor (GM-CSF), IL-3, Kit Ligand (KL), erythropoietin (Epo) or IL-2 to thereby increase the number of bone marrow cells. The bone marrow cells, cultured in vitro, then can be administered to a mammal to stimulate the proliferation of additional bone marrow cells. Alternatively, the stimulated cells can be administered directly to a mammal having a compromised bone marrow cell population to generate bone marrow cells in vivo.

BRIEF DESCRIPTION OF THE DRAWINGS

FIG. 1 illustrates the LAK activity (% cytotoxicity) of a $CD8^+$—depleted PBL population, $CD4^+$—depleted PBL population, and unseparated PBLs, stimulated with the anti-CD3 MoAb OKT3 and continuously cultured with IL-2.

FIG. 2 illustrates the LAK activity (% cytotoxicity) of: (a) a $CD4^+$—depleted PBL population stimulated with the anti-CD3 MoAb OKT3 and continuously cultured with IL-2; (b) the $CD8^+$ cells isolated from the cultured $CD4^+$—depleted PBLs; and (c) the remaining $CD4^-CD8^-$ cell population isolated from the cultured $CD4^+$—depleted PBLs.

FIG. 3 illustrates the LAX activity (% cytotoxicity) of: (a) a $CD8^+$—depleted PBL population stimulated with the anti-CD3 MoAb OKT3 and continuously cultured with IL-2; (b) the $CD4^+$ cells isolated from the cultured $CD8^+$—depleted PBLs; and (c) the remaining $CD4^-CD8^-$ cell population isolated from the cultured $CD8^+$—depleted PBLs.

FIG. 4 illustrates the LAX activity (% cytotoxicity) of: (a) an undepleted, i.e., unseparated or total, PBL population stimulated with the anti-CD3 MoAb OKT3 and continuously cultured with IL-2; (b) the $CD4^+$ cells isolated from the cultured undepleted PBLs; (c) the $CD8^+$ cells isolated from the cultured undepleted PBLs; (d) $CD4^+$ cells isolated from a cultured $CD8^+$—depleted PBL population; and (e) $CD8^+$ cells isolated from a cultured $CD4^+$—depleted PBL population.

DETAILED DESCRIPTION OF THE INVENTION

Figure 5A:
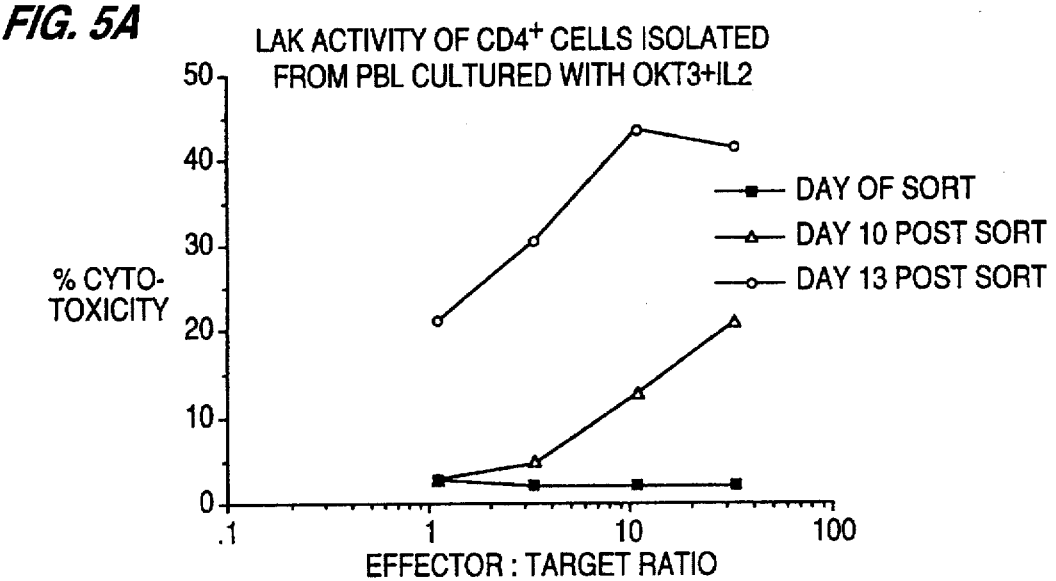
FIGS. 5A and 5B illustrate the LAX activity (% cytotoxicity) of $CD4^+$ and $CD8^+$ cells, respectively, isolated from cultured (OKT3+IL-2) undepleted PBL populations and subsequently cultured with IL-2 alone. This data was obtained after five days of culturing the undepleted PBLs, i.e., "day of sort," and after ten and thirteen days of culturing each cell subset in IL-2.

As used herein, the phrase "depletion method" denotes a method of enhancing the immunotherapeutic activity of an immune cell population by utilizing a "depleted immune cell population." A depleted immune cell population is the portion of the immune cell population remaining after at least one cell subset, or subpopulation, that is capable of down-regulating the immunotherapeutic activity of that immune cell population has been separated and removed therefrom. The resulting depleted immune cell population, when stimulated, is referred to herein as a "stimulated immune cell population." Throughout this description, the phrase "positive selection method" denotes a method of enhancing the immunotherapeutic activity of an immune cell population by using an "immune cell subset." An immune cell subset is the portion of the immune cell population that has been separated and removed, or panned, from the immune cell population. This immune cell subset, when stimulated, is referred to herein as a "stimulated immune cell subset".

As used herein, LAK activity is defined as the ability of lymphocytes to lyse tumor cells, and to a lesser degree normal cells. This activity in lymphocytes is typically stimulated by lymphokines, such as IL-2. In the in vitro examples herein, LAK activity refers to the ability to lyse the human NK-resistant tumor target, HL60. NK activity is defined as the ability to lyse tumor cells, but not normal cells, which does riot result from prior stimulation. In the in vitro examples used herein, NK activity refers to the ability to lyse the human tumor line K562. Since similar results were obtained with both tumor lines, only the LAK results with HL60 are shown. In the in vivo examples used herein, LAK and NK activity refers to the ability to reduce the tumor volume.

The immune cell population can include all immune cells that are part of an immune system, such as T cells, B cells, NK cells, and macrophages. Any of these cells, or a combination of these cells, can be depleted by the method of the present invention, with a resultant increased immunotherapeutic, e.g., antitumor, effect. As used herein, the "immune cell population" can be, and is preferably, a total, i.e., unseparated or undepleted population as obtained from a whole blood sample; however, the "immune cell population" can be any portion of a total population that contains a cell subset or subpopulation that down-regulates the immunotherapeutic activity of the larger population, or is capable of developing immunotherapeutic activity itself.

As used herein, "depleted immune cell population" preferably refers to a total cell population derived from a sample of whole blood, spleen, lymphnode, tumor infiltrating lymphode, and the like, with at least one cell subset or subpopulation, which down-regulates the immunotherapeutic activity of the total population, removed therefrom. Alternatively, however, "depleted immune cell population" can be a subpopulation or subset itself, which upon further removal of a cell type can exhibit an enhanced immunotherapeutic activity.

As used herein, "culturing" indicates the process whereby cells are placed in a tissue culture medium comprising nutrients to sustain the life of the cells, and other additives, such as the growth factor IL-2. This process can take place in any vessel or apparatus. The process can involve various stages of culturing and subculturing. Typically, cells are initially cultured and expanded, i.e., increased in size and number. These expanded cells are then counted and divided into groups, or subcultures, for further culturing and expansion. The expanded cells from each of these subcultures are then divided into additional subcultures, for further culturing and expansion. Each of the culturing or subculturing steps typically lasts about 48 hours, with fresh tissue culture medium used in each culture.

As used herein "immunotherapeutic activity" refers to any of a variety of immune responses of immune cells. This includes a cytotoxic or antitumor effect. As used herein "cytotoxicity" includes specific lytic activity, and the nonspecific lyric activity of lymphokine activated killer (LAK) cells and natural killer (NK) cells in vitro. As used herein, "antitumor activity" includes specific lyric activity, and the nonspecific lytic activity of lymphokine activated killer (LAK) cells and natural killer (NK) cells both in vitro and in vivo. In general, the methods of the present invention are preferably directed to enhancing the antitumor activity of immune cells, preferably T lymphocytes.

Preferably, the method of enhancing the immunotherapeutic activity of an immune cell population involves first depleting a T lymphocyte subpopulation, e.g., PBL populations, before the initiation of culture with an antibody to a lymphocyte surface receptor, optionally with IL-2. Initial culturing with only an antibody to a lymphocyte surface receptor, and optionally with a relatively minor amount of IL-2, is advantageously utilized in the present invention.

As used herein, the phrase "relatively minor amount of IL-2" denotes a stabilizing amount of IL-2, i.e., an amount sufficient to sustain the culture at about its initial cell density. Advantageously, IL-2 is present in an amount of less than about 30% of the mount of IL-2 typically used in culturing procedures. When immune cells are cultured optionally in the presence of IL-2, this typically will mean that if IL-2 is used at all, it is used in a "relatively minor amount." For example, if about 1,000 units of IL-2 typically are used in culturing a specific immune cell population, then less than about 300 units would be used in the present invention if culturing with IL-2 is optional, and IL-2 is utilized. Advantageously, IL-2 is not used in the initial culturing process with the antibody to a lymphocyte surface receptor. In addition, the immune cell subsets usually are advantageously $CD4^+$ or $CD8^+$ lymphocytes, or more specific subsets of each of these populations.

As a result of the removal or depletion of specific cell subsets that inhibit antitumor activity, the remaining immune cells, i.e., depleted immune cell population and immune cell subsets, preferably develop increased immunotherapeutic activity as represented by an ability to reduce tumor volume in vivo. The cytotoxic activity of the cultured NK cells can in some situations also be increased above that of uncultured NK cells by the methods of the present invention. Thus, the stimulated depleted immune cell population and stimulated immune cell subsets preferably develop an increased immunotherapeutic activity as represented by an ability to reduce tumor volume, i.e., antitumor activity, when compared to a similarly treated undepleted immune cell population.

To effectuate this enhanced immunotherapeutic activity, e.g., increased antitumor activity, the initial culturing processes described above of either the immune cell populations or the depleted immune cell populations preferably occur over a period of about two days. The culturing process can occur over a period of at least about ten days, but a period of less than 48 hours is more advantageous, and most advantageously, less than about 24 hours. According to an embodiments of the invention for enhancing the cytotoxicity in vitro, the culturing process involves: stimulating a depleted immune cell population or an immune cell subset with an antibody to a lymphocyte surface receptor during the first 48 hours of culturing in a first medium that also optionally contains a relatively minor amount of IL-2; removing the stimulated depleted immune cell population or stimulated immune cell subset from the first medium; and optionally subculturing the stimulated depleted immune cell population or stimulated immune cell subset in a second medium that contains IL-2 without any additional amount of an antibody to a lymphocyte surface receptor. Additional subculturing of the stimulated depleted immune cell population or stimulated immune cell subset is not required, however, for enhancing the immunotherapeutic activity in vivo since the cells are typically administered to a mammal shortly after stimulation.

The antibody to a lymphocyte surface receptor can be any of a variety of monoclonal antibodies against a surface antigen receptor complex. Advantageously, the antibody to a lymphocyte surface receptor is an anti-CD3 MoAb, i.e., an antibody against the antigen receptor complex CD3, such as OKT3. Additional useful antibodies include an anti-CD2, anti-CD4, anti-CD5, anti-CD28, anti-CD11b, etc., monoclonal antibody (MoAb). The antibodies can be used alone or in various combinations with other antibodies. For example, anti-CD3 can be used in combination with anti-CD2, anti-CD4, anti-CD5, anti-CD28, or anti-CD11b, for effective results. Anti-CD3 or anti-CD2 can each be used individually as the antibody in the cultures. The anti-CD3 MoAb can be, but is not limited to, OKT3, WT32, Leu-4, SPV-T3c, RIV9, 64.1, etc. More preferably, the anti-CD3 MoAb is OKT3, which is available from Ortho, a division of Johnson & Johnson.

An additional method useful in enhancing the immunotherapeutic activity of an immune cell population comprises (i) first culturing an immune cell population to form a cultured immune cell population; (ii) separating a cell subset, or subpopulation, that is capable of developing immunotherapeutic activity, e.g., cytotoxicity to form a stimulated depleted immune cell population or a stimulated immune cell subset; and optionally (iii) separately culturing, i.e., subculturing, the stimulated depleted immune cell population or a stimulated immune cell subset in a second medium in the presence of IL-2.

Preferably, by using this method, the immunotherapeutic activity, as represented by the ability to reduce tumor volume, of this subpopulation is enhanced when compared to a similarly treated undepleted cell population. In addition, the separated cells preferably are $CD4^+$ or $CD8^+$ lymphocytes, or subsets of each of these populations.

To effectuate the enhanced immunotherapeutic activity, e.g., increased antitumor activity, of immune cell subpopulations prepared in accordance with the methods described above, the initial culturing process preferably involves the use of IL-2 and an antibody to a lymphocyte surface receptor to produce what is referred to as CD3-LAK cells or T-activated killer cells (T-AK). The initial culturing process of the unseparated or undepleted, i.e., total, immune cell populations can occur over a period of at least about three days, and possibly at least about five days. Alternatively, the initial culturing process can involve stimulation by an antibody to a lymphocyte surface receptor and thereafter cultured With IL-2; however, culturing with IL-2 may riot be necessary. In either of above mentioned scenarios, the initial culturing can occur over a period of less than about 48 hours, and more advantageously less than about 24 hours. The optional subsequent subculturing process in IL-2 of each cell subset preferably occurs over a period of at least about three days, and more preferably at least about ten days.

To decrease the tumor volume in a mammal having tumors, the immunotherapeutic activity of an immune cell population first is enhanced in accordance with any of the methods described above. This stimulated depleted immune cell population or stimulated immune cell subset then is administered to a mammal having tumors. Optionally, the mammal is pretreated with an immunosuppressant that preferably also is chemotherapeutic. While not intending to be bound by any theory, the use of an immunosuppressant may serve to suppress the activity of other immune cells thereby permitting the stimulated cells to function more effectively upon administration to the mammal or the immunosuppressant may serve to diminish the total volume of the tumor. Usually, immunosuppressants such as doxorubicin or cyclophosphamide (CYTOXAN™) are used, although those skilled in the art readily recognize that other immunosuppressants can be used in accordance with the present invention.

The stimulated depleted immune cell population or stimulated immune cell subset advantageously is added to the mammal with liposomal IL-2. More advantageously, the stimulated immune cells are administered intravenously whereas the liposomal IL-2 is administered intraperitoneally. Usually, liposomal IL-2 is added periodically after the initial administration of the stimulated depleted immune cell population or stimulated immune cell subset. In addition, the liposomal IL-2 and the stimulated depleted immune cell population or stimulated immune cell subsets can be administered to the mammal a second time after the initial treatment. Preferably, the second treatment takes place about 1 week after the initial treatment, although a second treatment any time after about 4 days is effective in substantially eradicating the tumor. As used herein, the phrase "substantial eradication of tumor" denotes a reduction in tumor volume to a point where the tumor either is completely destroyed or is so small that it is not readily recognizable by conventional methods.

Mammals that have been treated in accordance with the procedures outlined above are immunized against recurring tumors. Mammals that are treatable in accordance with the present invention include, but are not limited to, mice, rats, farm animals and pets, primates and humans, etc. Advantageously, mammals that have received an initial and a second treatment of liposomal IL-2 and stimulated depleted immune cell population or stimulated immune cell subsets having enhanced immunotherapeutic activity, resist and substantially eradicate tumors that are subsequently introduced. These mammals therefore are immunized against the original tumor and tumors similar to it.

The aforementioned immunity also can be transferred to other mammals. Particularly, splenocytes extracted from a mammal that has been treated with liposomal IL-2 and a stimulated depleted immune cell population or stimulated immune cell subset having enhanced immunotherapeutic activity are useful in immunizing other mammals. Those skilled in the art are capable of extracting splenocytes from the spleen of a mammal by using conventional procedures. In addition, those skilled in the art are capable of separating various immune cell populations such as T and B cells, from separated splenocytes.

Advantageously, splenocytes are removed from the spleen of a mouse that has been immunized in accordance with the aforementioned procedures. These cells then are administered to a second mouse. This second mouse then develops an immune response to the same or similar tumors when challenged. For example, splenocytes from a mouse that developed antitumor activity by virtue of the aforementioned immunization procedures with respect to, e.g., MC-38 tumor, can be administered to a second mouse. If this second mouse is challenged with the MC-38 tumor, the mouse will be capable of reducing the size of, and substantially eradicating the tumor. The present invention therefore utilizes a transferable immunity protocol to transfer the immunity of one mammal to another mammal with respect to tumors.

The IL-2 employed in culturing the depleted cell populations or the undepleted populations typically is free IL-2. The IL-2 utilized when administering the stimulated depleted cell populations to a mammal, however, advantageously is liposomal IL-2. Liposomal IL-2 is utilized because it provides a longer lasting, more controlled and substantial release of the IL-2, thereby mitigating the toxicity of the IL-2 and reducing disadvantageous side attendant upon its use.

Mammals undergoing bone marrow engraftment have a compromised bone marrow cell population for a period of about 15 to about 25 days. Throughout this description, the term "compromised bone marrow cell population" denotes an incomplete or depleted bone marrow cell population when compared to the mammal's normal bone marrow cell population. For example, a compromised bone marrow cell population can include a bone marrow cell population that is insufficient to achieve homeostasis in the mammal's immune system. The present invention therefore advantageously further provides a method of stimulating the proliferation of bone marrow cells to generate bone marrow cells more readily in a compromised bone marrow cell population.

In accordance with this method, the immunotherapeutic activity of an immune cell population is enhanced in accordance with one of the four procedures outlined above. Preferably, the immunotherapeutic activity is enhanced by culturing positively selected CD4$^+$ cells in the presence of anti-CD3 and IL-2 for a period of at least 24 hours. More preferably, the CD4$^+$ cells are cultured in the presence of anti-CD3 and IL-2 for the first 24 hours, and then additionally cultured in the presence of IL-2, and optionally anti-CD3 for at least an additional 48 hours. The resulting stimulated depleted immune cell population or stimulated immune cell subset is capable of stimulating the proliferation of bone marrow cells as defined, for example, by an increase in the number of colony forming units.

Alternative methods of stimulating the production of bone marrow cells can be carried out in accordance with the present invention. First, bone marrow cells can be extracted and purified from a mammal using techniques well known in the art, and then incubated with the stimulated depleted immune cell population or stimulated immune cells subset for a period of time sufficient to generate bone marrow cells. Preferably, the cells are incubated for a period of about 10 to about 20 days and most preferably, about 14 days at about 37° C. In addition, cytokines such as GM-CSF, IL-3, KL and Epo can be added to the bone marrow during culturing. Kit Ligand (KL) is a soluble factor, like IL-2, that is known in the art, and is being useful in the stimulation of early growth and progression of progenitor cells during bone marrow engraftment. Obtaining and using KL within the confines of the present invention is within the routine skill of those skilled in the art upon reading the present specification. While not intending to be bound by any theory, it is believed that the addition of one or more of the cytokines described above (GM-CSF, IL-3, KL, and the like) to the bone marrow provides a synergistic proliferative effect. The bone marrow cells produced in accordance with this method then can be infused into a mammal having a compromised bone marrow cell population using known techniques, particular, by intravenous injection. Also, the bone marrow cells may be injected at the same time as the stimulated depleted immune cell population or stimulated immune cell subset during a bone marrow transplant such that the stimulated cells stimulate the proliferation of additional bone marrow cells.

Alternatively, the stimulated depleted immune cell population or stimulated immune cell subset can be administered to a mammal having a compromised bone marrow cell population using known techniques, e.g., intravenous injection. Optionally, the mammal is pretreated with an immunosuppressant such as CYTOXAN, that preferably also is chemotherapeutic. Advantageously, the stimulated depleted immune cell population or the stimulated immune cell subset is administered periodically to the mammal, for example, every four or five days. More advantageously, the stimulated depleted immune cell population or stimulated immune cell subset is administered with an additional cytokine such as IL-2, IL-3, GM-CSF, KL, Epo, and the like. The administration of the stimulated depleted immune cell population or stimulated immune cell subset serves to stimulate the proliferation of additional bone marrow cells in a compromised bone marrow cell population of the treated mammal to generate bone marrow cells more rapidly when compared to proliferation of an unstimulated compromised bone marrow cell population.

DEPLETION OF CELL SUBPOPULATIONS

The depletion of at least one cell subset, or subpopulation, such as $CD4^+$, or $CD8^+$ cells, or specific subsets of either of these cell populations, that is capable of down-regulating (i.e., preventing the effector cells from developing the immunotherapeutic, e.g., cytolytic, machinery) the immunotherapeutic activity of an immune cell population, from the total immune cell population results in the development of enhanced immunotherapeutic activity, as represented by an increased antitumor effect. The cells may be depleted from a naive total immune cell population or from a total immune cell population that has been stimulated. Specifically, the depletion of a T lymphocyte subpopulation, that inhibits the antitumor activity of a total immune cell population, from the total immune cell population results in the development of high levels of LAK activity in the remaining "depleted" immune cells. Advantageously, depletion of a T lymphocyte subpopulation that inhibits the antitumor activity of a total immune cell population from the total immune cell population, and then stimulation of the depleted cell subpopulation results in the development of high levels of LAK activity in the stimulated depleted immune cell population.

This effect occurs in response to culturing the depleted immune cell population, (or whole cells that are to be depleted), in the presence of an antibody to a lymphocyte surface receptor, optionally in the presence of interleukin-2 (IL-2). Preferably, this occurs in response to initial stimulation with an antibody to a lymphocyte surface receptor and continuous culturing, or subculturing, in the presence of IL-2 for in vitro efficacy. Those skilled in the art will recognize, however, that for in vivo efficacy, additional culturing in the presence of IL-2 is not necessary since the stimulated depleted cell population will be administered directly to the mammal, along with IL-2.

For in vitro efficacy, the cells preferably are cultured in a first tissue culture medium the lymphocyte surface receptor antibody, optionally with IL-2. Thereafter, the cells are cultured, or subcultured, in a second tissue culture medium with IL-2 but without any additional amount of an antibody to a lymphocyte surface receptor. Further cultures, or subcultures, in the presence of IL-2 can also occur. Alternatively, the cells can be stimulated with an antibody to a lymphocyte surface receptor alone, and then optionally cultured with IL-2 without further culturing with IL-2.

Although the lymphocyte surface receptor antibody is preferably not added to any of the subcultures after the first 48 hours, it can be present in subsequent subcultures if the cultured cells from the first culture are not washed before the addition of a second tissue culture medium containing IL-2 without any surface receptor antibody. Any protocol, however, for culturing immune cells in which the immune cells are in the presence of both IL-2 and an antibody to a lymphocyte surface receptor at any time and for any period of time in the overall course of the culturing process is also within the scope of the present invention. Furthermore, any protocol in which immune cells are stimulated with the antibody alone in the tissue culture media without any further IL-2 culturing is within the scope of the present invention.

In the present invention, for maintaining the in vitro viability, the cells (depleted immune cell population) preferably are cultured with IL-2 for at least about 2 days, more preferably for at least about ten days. Similar results have been obtained from cells cultured in the presence of IL-2 for as long as 30 days, with subculturing occurring approximately every 48 hours. As stated above, the cells are preferably stimulated with an antibody to a lymphocyte surface receptor during the first 48 hours of culture, and preferably, only for the first 24 hours.

For in vivo efficacy, however, the depleted immune cells typically are cultured in the presence only of an antibody to a lymphocyte surface receptor for less than about 48 hours, preferably less than about 24 hours. If IL-2 is added during the initial culturing period, only a relatively minor amount of IL-2 is added. Advantageously, less than about 100 units/ml of IL-2 is added during this initial culturing period. After the initial culturing period, if the stimulated depleted immune cell population is to be maintained in vitro, the presence of additional IL-2 is advantageous to maintain and possibly grow the stimulated depleted cell population or stimulated cell subpopulation. After the initial culturing period, if the stimulated depleted immune cell population is administered in vivo to a mammal, then additional culturing with IL-2 is not required.

The interleukin-2 (IL-2) is a commercially available T cell growth factor. It can be a naturally occurring IL-2 or it can be recombinant IL-2. It is believed that other lymphokines can also be used in .the present invention to provide the lymphokine activated cells. These include IL-1, IL4, IL-6, interferons, etc. It is envisioned that they can be used alone, in sequence, or in combination with IL-2 in the culturing media. The liposomal interleukin-2 (IL-2) preferably administered in vivo is the commercially available T cell growth factor, only encapsulated in a liposome.

The immune cells, preferably T lymphocytes, and more preferably peripheral blood mononuclear lymphocytes can be depleted of specific T cell subsets by any method. The depletion can take place either before the initial culturing with an antibody to a lymphocyte surface receptor and, optionally IL-2 or after the initial culturing of whole cells. Preferably, the PBLs are depleted of specific subsets by negative depletion using magnetic beads. Typically; this involves the labelling of the PBLs with an antibody to a lymphocyte surface receptor for the T cells that are to be removed from the total PBL population. This mixture of labelled and unlabelled cells are then mixed with goat anti-mouse IgG-coated magnetic beads. A complex of the beads and the labelled T cells, i.e. , those cells complexed with the surface receptor antibody, is formed. The beads/ labelled T cell complexes are then separated from the mixture using a magnetic separator. In this way, a specific T cell subset, or portion thereof, can be removed from the PBL mixture.

The specific immune cell subset removed can be any that down-regulates the immunotherapeutic activity, preferably the cytotoxic activity, of the total immune cell population. The removed subsets can include: $CD4^+$, or any of its subsets such as 2H4 or 4B4; $CD8^+$, or any of its subsets; NK cells, or any of its subsets; macrophages; B cells; and the like. Preferably, the immune cell subsets removed are T cell subsets, and more preferably they are $CD4^+$ or $CD8^+$ cells.

In general, a typical sample of PBLs from a sample of human whole blood contains about 20–30% $CD8^+$ cells and about 30–50% $CD4^+$ cells. In order to increase the immunotherapeutic activity, e.g, antitumor activity, of an immune cell population according to the present invention, the cells that inhibit or down-regulate the immunotherapeutic activity of the population need only be removed until an increase in the immunotherapeutic activity is observed in the remaining cell population. Preferably, in order to increase the immunotherapeutic activity of immune cells according to the present invention, the number of $CD4^+$ or $CD8^+$ cells are reduced in the depleted immune cell populations by at least about 75%, more preferably by at least about 90%. Most preferably, however, a "substantially completely depleted" immune cell populations, e.g., PBL populations, contain less than about 5 % of the cell subset removed. For example, a "substantially completely $CD4^+$—depleted immune cell population" contains less than about 5% $CD4^+$ cells. Thus, the method of the present invention includes separating preferably at least about 75 %, and more preferably at least about 90% of the $CD4^+$ or $CD8^+$ cells from PBLs to increase the immunotherapeutic activity, e.g., antitumor activity, of the remaining depleted immune cell population.

The increased immunotherapeutic activity of the immune cell populations is determined in vivo by the ability of immune cells to reduce or substantially eradicate a tumor target. Antitumor activity can be determined in vitro, however, by a comparison of the level of radioactivity released in tissue culture media from the effector/target combination to the level of radioactivity in the culture media released from the target alone. Thus, increased immunotherapeutic activity of immune cells can be demonstrated by an increase in the percent cytotoxicity of the effector cells on human tumor cells in vitro, however, in vivo efficacy in mammals is preferred. The human tumor cell lines useful in determining in vitro efficacy can be any of a variety of cell lines commercially available, including leukemia cells and fresh tumor targets, preferably, leukemia cells. Advantageously, however, the antitumor activity of stimulated depleted immune cell populations or stimulated cell subpopulations is determined in vivo by an ability of the cells to decrease or substantially eradicate tumor volume.

As can be seen from FIG. 1, the mount of cytolytic activity of either the $CD4^+$—depleted or the $CD8^+$—depleted cultures is greater than that of unseparated, i.e., total or undepleted, PBLs regardless of the effector to target ratio. The LAK activity was measured at several time points between 10 and 30 days of culture, with similar results regardless of the day of assay. Similar results are obtained with $CD4^+$—depleted and $CD8^+$—depleted populations in about three to five day cultures. Shorter culturing time periods, i.e., on the order of less than 48 hours, however, are capable of producing similar results.

These observations could be explained in several manners. For example, the enhanced LAK activity could be the result of a relative enrichment in $CD3^-CD16^+$ and/or $CD56^+$ NK cells, or $CD3^+CD4^-CD8^-$ (γδ) T cells, both of which have been previously shown to mediate LAK activity. It has been determined, however, that the enhanced LAK, as well as NK activity, is preferably the result of the activation of the cell subpopulations, i.e., $CD4^+$ or $CD8^+$ T cells, that remain in the depleted cultures.

This was determined by labelling the cells from the depleted PBL populations with anti-CD8 MoAb (in the $CD4^+$—depleted cultures) or anti-CD4 MoAb (in the $CD8^+$—depleted cultures), and positively sorting them using a fluorescence-activated cell sorter (FACS). When cells from $CD4^+$—depleted cultures are separated into $CD8^+$ and $CD4^-CD8^-$ populations, and tested for LAK and NK activity immediately after sorting, both $CD8^+$ cells and $CD4^-CD8^-$ cells mediate significant levels of LAK and NK activity.

As shown in FIG. 2, the $CD4^-CD8^-$ cells demonstrate about 65% cytotoxicity at an effector to target ratio of about 30:1. The $CD8^+$ cells demonstrate about 40% cytotoxicity at an effector to target ratio of about 30:1. Similar results are observed when $CD8^+$—depleted populations are labelled with anti-CD4 MoAb and sorted into $CD4^+$ and $CD4^-CD8^-$ populations (FIG. 3). Additional phenotyping of the $CD4^-CD8^-$ cells in both types of cultures show them to be primarily $CD16^+Leu19^+$ or $CD3^+CD4^-CD8^-$.

In comparison, however, when cultured with IL-2 and an antibody to a lymphocyte surface receptor in an undepleted population of PBLs, isolated $CD4^+$ or $CD8^+$ cells do not necessarily develop such significant levels of NK or LAK activity. As can be seen by the results shown in FIG. 4, at an effector to target ratio of about 10:1, the cytotoxicity of $CD4^+$ or $CD8^+$ cell subsets is no more than about 10–15%, and at an effector to target ratio of about 30:1, the eytotoxieity of $CD4^+$ or $CD8^+$ cell subsets is no more than about 15–20 %.

Results similar to those shown in FIG. 4 were obtained at various times between 10 and 30 days of culturing undepleted PBLs with IL-2 and the anti-CD3 MoAb OKT3. The $CD4^+$ and $CD8^+$ cells were isolated by negative depletion, however it is also possible to isolate them by positive FAGS selection. Control cultures of $CD4^+$—depleted or $CD8^+$—depleted cells were sorted to obtain $CD8^+$ and $CD4^+$ cells, respectively. As shown in FIG. 4, $CD8^+$ and $CD4^+$ cells from the depleted cultures developed significant levels of LAK activity, i.e., at least about 40% cytotoxie activity at an effector to target ratio of about 30:1. Thus, although $CD4^+$ and $CD8^+$ cells do not show significant LAK or NK activity when tested immediately after isolation from CD3-LAK cultures, $CD4^+$ and $CD8^+$ cells can develop high LAK activity if one of these subsets is depleted from the PBL population prior to the initiation of culture and then stimulated to form a stimulated cell subpopulation. Advantageously, stimulated cell subpopulations are used in accordance with the depletion method described above.

Although not intending to be limiting in any manner, these results suggest that the development of LAK activity by T cells subpopulations is inhibited in the PBL cultures. It is believed that this inhibitory effect is the result of T cells, and possibly other immune cells, such as macrophages or B cells, that prevent the development of LAK activity by the other T cell subsets. Furthermore, it is believed that the inhibitory T cells generally exert their effect only if present throughout the entire culture period.

POSITIVE SELECTION OF CELL SUBSETS

Cell subpopulations, such as $CD4^+$ or $CD8^+$ cells, or specific cell subsets of these populations, separated from CD3-LAK cells, i.e. , T-AK cells, show negligible LAK activity. These T-AK cells are typically cultured in the presence of an antibody to a lymphocyte surface receptor and, optionally IL-2 for about five days. However, these cell subsets can be removed from the T-AK cells and then cultured in the presence of an antibody to a lymphocyte surface receptor and, optionally IL-2. It has been determined that if the $CD4^+$ and $CD8^+$ cells are subsequently cultured separately in the presence of IL-2 alone, each individual population rapidly develops LAK activity stimulated depleted immune cell population or stimulated immune cell subset in vitro.

Initial culturing of unseparated PBL populations preferably occurs over a period of at least about three days, and more preferably at least about five days. Initial culturing of positively selected cells selected from an unseparated PBL population that has or has not first been cultured for less than 48 hours, preferably less than 24 hours, also is within the scope of the present invention. The subsequent culturing process in IL-2 of each cell subset preferably occurs over a period of at least about three days, and more preferably at least about ten days. The subsequent culturing process can be carried out for up to about 30 days. For in vivo applications, however, subsequent culturing in the presence of IL-2 for extended periods of time is not necessary; rather the separated cell subpopulations from the stimulated PBL populations can be administered either directly to a mammal or administered after subsequent culturing with IL-2.

The subsequent culture of the separated CD4$^+$ and CD8$^+$ cell populations is done in the presence of preferably about 10–1000 units/ml IL-2, more preferably about 100–1000 units/ml IL-2. Initial culturing in the presence of an antibody to a lymphocyte surface receptor, optionally in the presence of a relatively minor amount of IL-2, typically is done in the presence of less than about 100 units/ml IL-2. Upon being tested for LAK activity at various times throughout the culturing process of the stimulated immune cell subsets, both populations rapidly develop and maintain high levels of NK and LAK activity.

Specific immune cells, preferably T lymphocytes, can be separated from an unseparated, i.e., total population of immune cells, preferably PBLs by any method. Preferably, the specific cell subpopulations are separated from the total populations by positive selection using fluorescence-labelled monoclonal antibodies. Typically, this involves adding a fluorescein isothiocyanate-conjugated MoAb or a phycoerythrin-conjugated MoAb to a cultured immune cell population, incubating the cells with the conjugate for 30 minutes at 4° C., washing the cells, and sorting or selecting out the labelled cells using a fluorescence-activated cell sorter. For positively selecting CD8$^+$ cells the monoclonal antibody OKT8 can be used, and for positively selecting CD4$^+$ cells the monoclonal antibody OKT4 can be used, both of which are available from the Ortho Division of Johnson & Johnson. In addition, murine CD4$^+$ and CD8$^+$ cell subpopulations of T cells can be separated by use of the murine monoclonal antibody counterpart, i.e., LY2.2 to separate CD4$^+$.

Figure 5B:
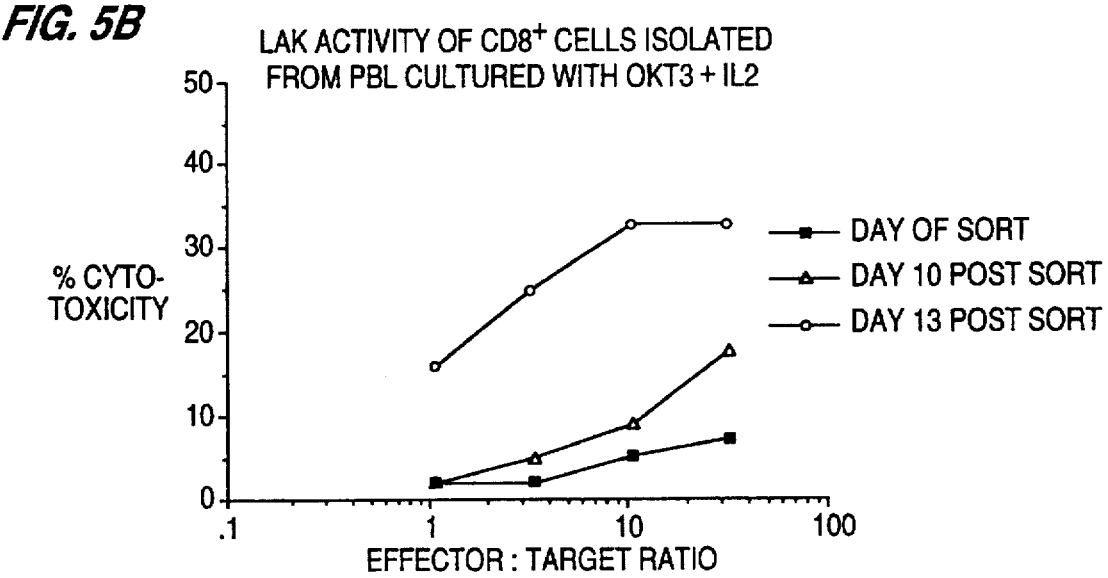

As can be seen in FIG. 5, both the CD4$^+$ and CD8$^+$ cell subsets show enhanced antitumor activity in vitro after ten days of culturing in IL-2. Although not shown, enhanced antitumor activity in vitro is seen after only three days of culturing in IL-2. Thus, using this methodology both CD4$^+$ and CD8$^+$ T cells can develop high levels of LAK activity.

Although this is in no way limiting, the results of the depletion and positive selection experiments suggest that the mutual inhibition involves some ongoing regulatory interaction between CD4$^+$ and CD8$^+$ cells that is effectively abolished once they are separated, and that it is not due to an event in the initial activation process. That is, the observation that either CD4$^+$ or CD8$^+$ T cells can rapidly acquire LAK activity once isolated from PBL cultures suggests that the absence of expression of LAK activity by these cells in the unseparated populations is not the result of an irreversible process. Rather, the inhibition requires the continued interactions by the reciprocal T cell subsets. Mixing experiments designed to test this hypothesis demonstrate that the maintenance of a suppressor effect requires the continued interaction of viable metabolically active T cell subsets.

The inhibition could be mediated through direct cell contact or via soluble factors. Regulatory networks have been described in which both T cell subsets must be present in order to obtain suppression of function [N. K. Damle et al., J. Exp. Med., 158, 159 (1983)]. These data suggest that there are inhibitory signals which prevent the development of LAX activity by CD4$^+$ or CD8$^+$ T cells in unseparated, i.e., total or undepleted, PBL populations. That is, there is a negative regulation of T cell function in PBL populations that appear to be mediated by the T cells themselves.

There are several soluble factors that might be involved in regulating the development of LAX activity by T cells, including interleukin-4 (IL-4) and transforming growth factor-$\beta$ (TGF-$\beta$). It is, of course, not necessary that both T cell subsets are regulated by the same factor.

IL-4 has been shown to inhibit both the growth and development of effector functions by LAX cells, although those effects appear to be principally on NK cells rather than T cells. See, for example, M. B. Widmer et al., J. Exp. Med., 166, 1477 (1987); H. Spits et al., J. Immunol., 141, 29 (1988); A. Nagler et al., J. Immunol., 141, 2349 (1988); Y. Kawakami et al., J. Exp. Med., 168, 2183 (1988). IL-4 is made primarily by CD4$^+$ T cells, which suggest that it could play a role in regulating the development of LAX activity in CD8$^+$ cells; however, this is not intended to be limiting in any way. See D. B. Lewis et al., Proc. Natl. Acad. Sci. USA, 85, 9743 (1988).

TGF-$\beta$ also has been shown to inhibit both NK and LAK activity. See, for example, A. Kasid et al., J. Immunol., 141, 690 (1988); and J. J. Mule et al., Cancer Immunol. Immunother., 26, 95 (1988). Furthermore, this inhibition has, in some cases, been shown to be based on the balance between the levels of IL-2 and TGF-$\beta$. See, for example, J. H. Kehrl et al., J. Exp. Med., 163, 1037 (1986).

The addition of human TGF-$\beta_1$ (TGF-$\beta$), which is available from R & D Systems, Minneapolis, Minn., to either CD4$^+$—depleted or CD8$^+$—depleted populations upon the initiation of the culturing process results in the inhibition of the lyric function of the depleted populations. Specifically, the addition of TGF-$\beta$ in concentrations ranging from 0.1–30 ng/ml upon initiating the culture, and during each of the subculturing steps, demonstrates a dose-dependent decrease in the lyric activity, i.e., LAK activity, of the T cells. This effect is reversible upon the removal of TGF-$\beta$ from the culture medium.

TGF-$\beta$ is produced by both CD4$^+$ and CD8$^+$ cells under certain culture conditions. Given that both T cell subsets produce TGF-$\beta$, it is possible that it is only when both CD4$^+$ and CD8$^+$ cells are present that the level of TGF-$\beta$ produced reaches the point were it has an inhibitory effect in the presence of high levels of IL-2. After depletion of either T cell subset, the levels of TGF-$\beta$ would be too low to have an inhibitory effect on the T cells; however, this is not intended to be limiting in any way.

The observations that either CD4$^+$ or CD8$^+$ cells can, under the appropriate conditions, develop LAK activity and that the generation of that LAK activity is regulated by the presence of the reciprocal T cell subset, have implications for protocols for adoptive immunotherapy. For example, under certain conditions it is preferable to have LAK activity mediated by T cells. Thus, the present invention includes using T cells with LAK activity for therapy in humans. Stimulated depleted cell populations or stimulated cell subpopulations can be used for immunizing humans against tumors and for transferring the immunity from one human to another. Such cells may possibly achieve complementary or different antitumor effects than have been observed in conventional protocols.

The following examples are set forth as representative of specific and preferred embodiments of the present invention.

These examples are not to be construed as limiting the scope of the invention in any manner. It should be understood that many variations and modifications can be made while remaining within the spirit and scope of the invention.

EXAMPLE 1

Isolation and Culture Of Cells with LAK Activity In Vitro

Peripheral blood lymphocytes (PBLs) were isolated from heparinized venous blood (human whole blood) by centrifugation over Ficoll-Hypaque according to the method of A. Boyum, Scand. J. of Clin. Lab. Invest., 99, 77 (1968), which is incorporated herein by reference. Isolated mononuclear cells were washed three times with phosphate buffered saline (PBS, pH 7.4) (GIBCO Laboratories, Grand Island, N.Y.) and counted. $CD4^+$ and $CD8^+$ enriched cultures were obtained by negative depletion using magnetic beads (obtained from Baxter Healthcare Corporation, Deerfield, Ill.; also available from Advanced Magnetics, Massachusetts; or Dynal Corp., Norway). Briefly, PBLs were labelled by incubation with either of the monoclonal antibodies OKT4 or OKT8 (Ortho, Raritan, N.J.) for 30 minutes on ice. The cells were then washed twice with cold PBS and mixed with goat anti-mouse IgG-coated magnetic beads (obtained from Baxter Healthcare; also available from Dynal Corp., Norway) at a bead:cell ratio of 10: 1. The bead/cell mixture was incubated for 30 minutes at 4° C. while rotating at 5–6 rpm. At the end of the incubation, the bead/cell suspension was diluted two-fold with cold PBS. Using a magnetic separator (Baxter Healthcare Corporation, Deerfield, Ill.), the beads were allowed to collect against the side of the test tube for five minutes. The supernatant containing unbound cells was then collected and transferred to a new tube. This process was repeated three times to completely remove the beads and bead-bound cells. The cells that remained in suspension ($CD4^+$—depleted or $CD8^+$—depleted PBLs) were washed and counted. This resulted in depleted PBL populations with less than about 5 % contamination by the T cell subset removed. The cells remained essentially unchanged during subsequent culture.

Peripheral blood lymphocytes or depleted populations ($5\times10^6$ cells) were cultured in 25 $cm^2$ flasks (Corning, Corning, N.Y.) in 10 ml tissue culture medium (TCM). The TCM consisted of Rosewell Park Memorial Institute (RPMF) 1640 medium (available from GIBCO, Grand Island, N.Y.) supplemented with 25 mM Hepes [N-(2-hydroxyethyl) piperazine-N'-(2-ethanesulfonic acid)], 2 mM L-glutamine, 100 units/ml penicillin, 100 µg/ml streptomycin (penicillin/streptomycin mix available from GIBCO, Grand Island, N.Y.), and 5% pooled heat-inactivated human serum. The cultures were supplemented with 1000 units/ml of highly purified recombinant human IL-2 from E. coli (Hoffman-LaRoche, Nutley, N.J.). [See, A. Wang et al., Science, 224, 1431 (1984); and S. A. Rosenberg et al., Science, 223, 1412 (1984), which are incorporated herein by reference]. The cultures were supplemented with 10 ng/ml of the anti-CD3 MoAb OKT3 (Ortho Division, Johnson & Johnson, Raritan, N.J.). The OKT3 was present in the culture during the first 48 hours. Thereafter, the OKT3 was diluted due to the addition of fresh TCM and IL-2. No additional OKT3 was added during the culturing process. Cultures were incubated at 37° C. in a humidified atmosphere of 5% $CO_2$. After the first 48 hours of culture, the cells were counted and subcultured at $0.5\times10^6$ cells/ml in TCM containing IL-2. Subsequently, the cells were counted and subcultured every 48 hours in fresh TCM with IL-2 at a concentration of $0.5\times10^6$ cells/ml.

EXAMPLE 2

Cell Sorting by Immunofluorescence

PBLs, $CD4^+$—depleted PBLs, or $CD8^+$—depleted PBLs were each cultured in OKT3+IL-2 as described above. At various times during the culture period, the cells were sorted on a fluorescence-activated cell sorter (FACS). PBL populations were labelled with fluorescein isothiocyanate- (FITC) conjugated or phycoerythrin- (PE) conjugated MoAb: OKT4 and OKT8 (Ortho). $CD4^+$—depleted populations were labelled with OKT8, and $CD8^+$—depleted populations were labelled with OKT4. The cells were incubated for 30 minutes at 4° C. and were then washed twice with cold PBS containing 2% fetal bovine serum. Cells were sorted on a FACS IV (Becton Dickinson, Mountain View, Calif.). Sorted cells were centrifuged and an aliquot restained to test the purity of the populations. All of the positively sorted populations used for determining LAK activity were more than 97% positive for the desired surface marker.

EXAMPLE 3

Cell-Mediated Lympholysis (CML) In Vitro

CML assays were done as described in S. -L. Wee et al., Hum. Immunol., 3, 45 (1981), which is incorporated herein by reference. Human tumor lines K562 (chronic myelogenous leukemia, obtained from American Tissue Type Culture Collection (ATTCC)) and HL60 (promyelocytic leukemia, ATTCC) were maintained in culture in RPMI 1640 with 10% fetal bovine serum (GIBCO, Grand Island, N.Y.). Cells were subcultured at $0.5\times10^6$/ml in fresh medium twice a week.

Cells of the line HL60 were not lysed by unstimulated PBLs and were therefore considered NK-resistant. LAK activity was measured as cytolytic against the NK-resistant targets HL60. NK activity was measured as cytolytic activity against the K562 targets.

Tumor cell line targets were labelled with 250–750 µCi of $Na^{51}CrO_4$ (5000 µCi/ml, New England Nuclear, Boston, Mass.) for one hour at 37° C. These cells were washed three times in TCM, resuspended in culture media that did not contain IL-2, counted, and aliquoted at 500 targets/well in a 96-well V bottom plate (Costar, Cambridge, Mass.) into which the effector cells, i.e., the peripheral blood lymphocytes or depleted populations cultured as described above in Example 1, had been previously aliquoted at set concentrations. The effector:target cell ratios ranged from 30:1 to 1:1. Plates were centrifuged at 65 g for five minutes and incubated in 5% $CO_2$ at 37° C. for four hours, after which 100 µl of media was harvested from each well into a scintillation vial with 2.5 ml of scintillation fluid (Biofluor, New England Nuclear, Boston, Mass.). Radioactivity was counted on a liquid scintillation counter (LKB, Turku, Finland).

Percent cytotoxicity was determined by the following equation (cpm=counts per minute):

$$\frac{\text{(experimental mean cpm)} - \text{(spontaneous release mean cpm)}}{\text{(maximal release mean cpm)} - \text{(spontaneous release mean cpm)}} \times 100$$

wherein "spontaneous release mean" is defined as the amount of $^{51}Cr$ released from target cells alone (background); "maximal release" is the total $^{51}Cr$ in the targets following lysis with a detergent such as Triton X-100; and "experiment mean" is the $^{51}Cr$ released in wells with targets and effectors.

Representative samples of the results of all in vitro experiments are displayed in FIGS. 1–5. Each data point in each figure represents an analysis of three separate samples analyzed after the same period of culture, i.e., between 10 and 30 days, and the same period of contact between the effectors and targets, i.e., about four hours.

EXAMPLE 4

Immunophenotyping

Cells ($1\times10^6$) were washed 3 times with HBSS after which they were incubated at 4° C. with 20 μl of the corresponding monoclonal antibody (OKT4 or OKT8 from Ortho, Rareton, N.J.). They were again washed 3 times with cold Hanks Balanced Saline Solution (HBSS) including 2% fetal calf serum and resuspended in 0.2% paraformaldehyde. Two color fluorescence measurements were performed on a Coulter Profile (Coulter Cytometry, Hialeah, Fla.) or a FACS IV (Becton Dickinson, Mountain View, Calif.).

EXAMPLE 5

Mixing Experiments $CD4^+$ or $CD8^+$ cells isolated from unseparated PBL T-AK cultures on day 5 were added at a 1:1 ratio into $CD4^+$—depleted, or $CD8^+$—depleted, populations, respectively, on day 0 of autologous cultures. Some of the cultures received irradiated cells. Lytic function was tested 4 days later as % cytotoxicity. The results as shown below in Table 1 demonstrated that the addition of nonviable irradiated cells did not prevent the development of lyric activity. However, the addition of non-irradiated, i.e., metabolically active, $CD4^+$ or $CD8^+$ cells completely suppressed the development of LAK activity by the $CD4^+$—depleted or $CD8^+$—depleted populations, respectively.

TABLE 1

$CD4^+$ and $CD8^+$ Cells From PBL Cultures Inhibits the Development of Lytic Function by $CD4^+$-Depleted and $CD8^+$-Depleted Cultures[a]

|  | % Cytotoxicity | | |
| --- | --- | --- | --- |
|  | 30:1 | 10:1 | 3:1 |
| $CD4^+$-Depleted | 38 | 26 | 15 |
| $CD4^+$-Depleted + $CD4^+$ from PBL | 4 | −1 | 1 |
| $CD4^+$-Depleted + irrad. $CD4^+$[b] | 42 | 26 | 11 |
| $CD8^+$-Depleted | 25 | 14 | 9 |
| $CD8^+$-Depleted + $CD8^+$ from PBL | −1 | 2 | −4 |
| $CD8^+$-Depleted + irrad. $CD8^+$[b] | 46 | 30 | 15 |

[a]$CD4^+$ and $CD8^+$ cells were positively sorted out of PBL stimulated with OKT3 + IL-2 and cultured for 5 days. The cells were added at a 1:1 ratio to autologous cultures which had been depleted of $CD4^+$ or $CD8^+$ cells, respectively. Lytic function was assayed on cell line HL60.
[b]Isolated $CD4^+$ and $CD8^+$ cells received 2500 rads.

EXAMPLE 6

Enhancing The Immunotherapeutic Activity

Of Cell Subpopulations In Vivo

Using Anti-CD3 Alone

The animal model used in the following experiments uses a tumor known as the MC-38 or MCA-38 murine carcinoma. Methods for using this animal model are well documented and are described in, for example, Lafreniere et al., MC-38 Adenocarcinoma Tumor Infiltrating Lymphocytes. . . . , J. SURG. ONCOL. 43:8–12 (1990); Johnkoski et al., Hepatic Metastasis Alters the Immune Function of Murine Liver Nonparenchymal Cells, ARCH. SURG. 127:1325–29 (1992); Lafreniere et al., Adoptive Immunotherapy of Murine Hepatic Metastases . . . . , J. IMMUNOL., 135:4273–80 (1985); and Papa et al., Antitumor Efficacy of Lytnphokine-Activated Killer Cells . . . . , CANCER RES. 46:4973–78 (1986). The disclosures of these documents are incorporated by reference herein in their entirety.

T-cells were purified from splenocytes which were removed from the spleen of a C57BL/6 mouse according to conventional procedures. See, Lafreniere (1985), supra. The purified T-cells were divided into two groups, and the first group of T-cells were not depleted.

The second group of T-cells were contacted with anti-CD8 (LY2.2) and passed over a cell purification column (R & D Systems from Minneapolis) to produce enriched $CD4^+$ cells. The first and second groups of T-cells (i.e., unseparated and $CD4^+$ cell subpopulation, respectively) were cultured with murine anti-CD3 (145-2C11) for a period of about 24 hours. The cells then were collected, washed and counted in accordance with the procedures outlined in the present specification.

C57BL/6 mice were injected with MCA-38 as described above, and had tumors which ranged from about 140 to about 220 $mm^3$. These mice initially were injected with 150 mg/kg/mouse CYTOXAN, an immunosuppressant and a chemotherapeutic agent, prior to immunotherapy with the cultured depleted and undepleted cells. Approximately 20 million stimulated $CD4^+$ and cultured undepleted cells per mouse were administered intravenously together with an intraperitoneal injection of about 50,000 units of liposomal IL-2. The volume of the tumors was measured after a period of 2, 5 and 8 days. The results are illustrated in FIG. 6.

Figure 6:
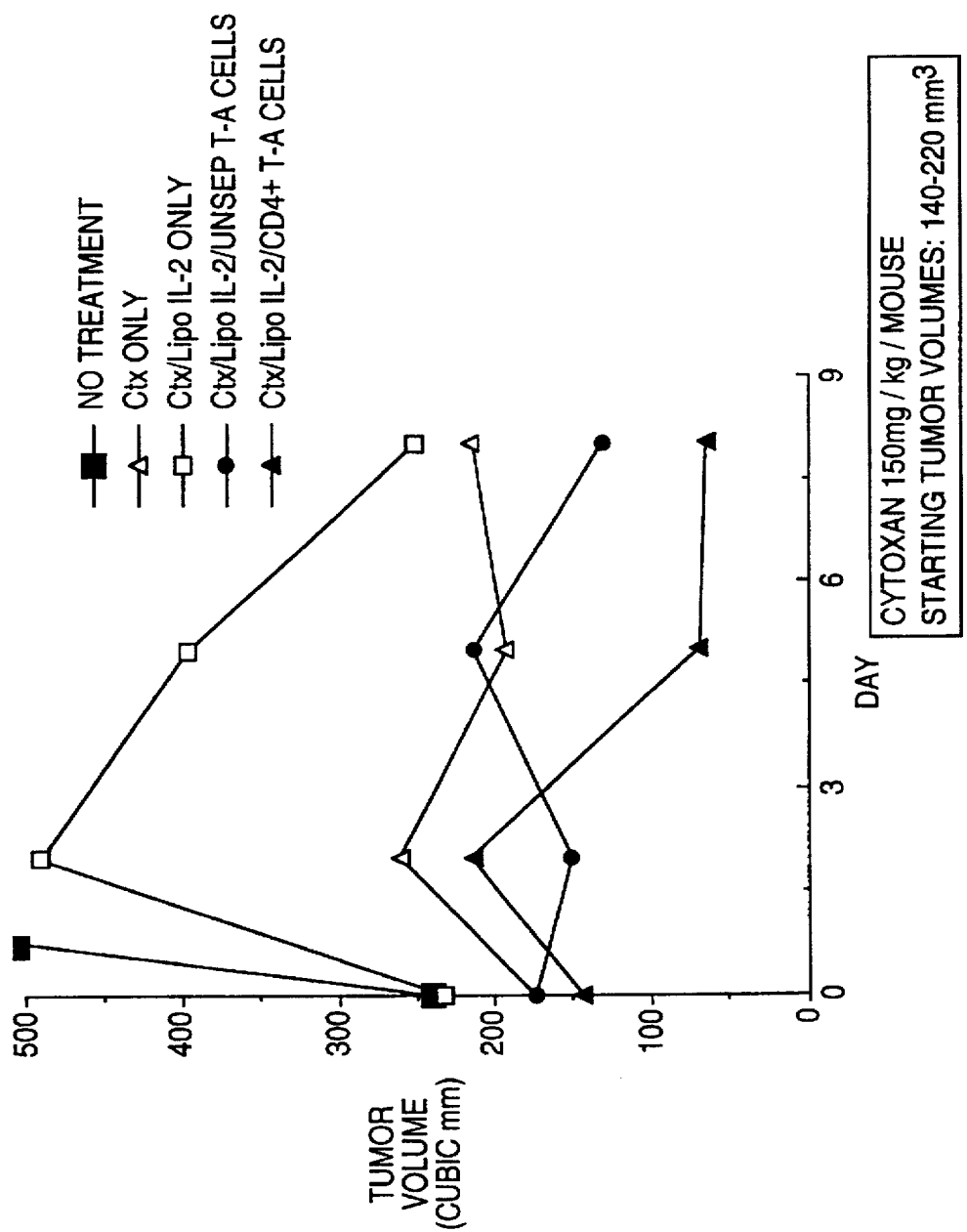
FIG. 6 illustrates the ability of stimulated $CD4^+$ cells to reduce tumor volume in vivo when stimulated only in the presence of anti-CD3 for less than 48 hours.

One group of the mice which had tumors ranging from 140 to about 220 $mm^3$ received no treatment (represented by the black box in FIG. 6), another group received injections of CYTOXAN only (represented by the empty triangle in FIG. 6). A third group of mice received CYTOXAN and liposomal IL-2 (represented by the empty box in FIG. 6), while a fourth group of mice received an intravenous injection of cultured undepleted cells, and an intraperitoneal injection of IL-2 (represented by the black circle in FIG. 6). The fifth group of mice represented the inventive group, and received an intravenous injection of cultured depleted cells and an intraperitoneal injection of liposomal IL-2 (represented by the black triangle in FIG. 6).

As can be seen from FIG. 6, the stimulated cell subpopulation cultured only in the presence of an antibody to a lymphocyte surface receptor for less than 48 hours, showed an enhanced anti-tumor immunotherapeutic activity when compared to similarly treated unseparated cells. One skilled in the art would reasonably expect that the stimulated immune cell subpopulation cultured in the presence of an antibody to a lymphocyte surface receptor for less than 48 hours would provide a similar result in humans.

EXAMPLE 7

Enhancing The Immunotherapeutic Activity

Of Cell Subpopulations In Vivo

Using Anti-CD3 And IL-2

$CD4^+$ cells and whole T cells were prepared in accordance with the procedures outlined in Example 6 above. The whole T-cells and the CD4+ cells were then stimulated in the presence of a murine anti-CD3 (145-2C11) and about 100 units/ml free IL-2 for a period of about 24 hours in a murine lymphocyte culture medium at a concentration of about 1.5 million cells per ml. The cells then were collected. Washed and counted in accordance with the procedures outlined in the present specification.

C57BL/6 mice were injected with MCA-38 as described above about 7 days prior to treatment with CYTOXAN, and had tumors which ranged from about 140 to about 220 mm$^3$. These mice initially were injected with 150 mg/kg/mouse CYTOXAN, an immunosuppressant and a chemotherapeutic agent, about four days prior to immunotherapy with the stimulated immune cell subsets and cultured undepleted cells. The stimulated CD4+ and undepleted T-cells were administered intravenously to the C57BL/6 mice affected with the MCA-38 tumor together with an intraperitoneal injection of about 50,000 units of liposomal IL-2. Intraperitoneal injections of liposomal IL-2 were repeated daily for about 4 days. About seven days after treatment with the stimulated immune cell subset and cultured whole cells, the mice that received the stimulated CD4+ cell subsets were again injected intravenously with stimulated CD4+ cells and with an intraperitoneal injection of liposomal IL-2. The volume of the tumors was measured periodically for a period of about 45 days. The results are illustrated in FIG. 7.

Figure 7:
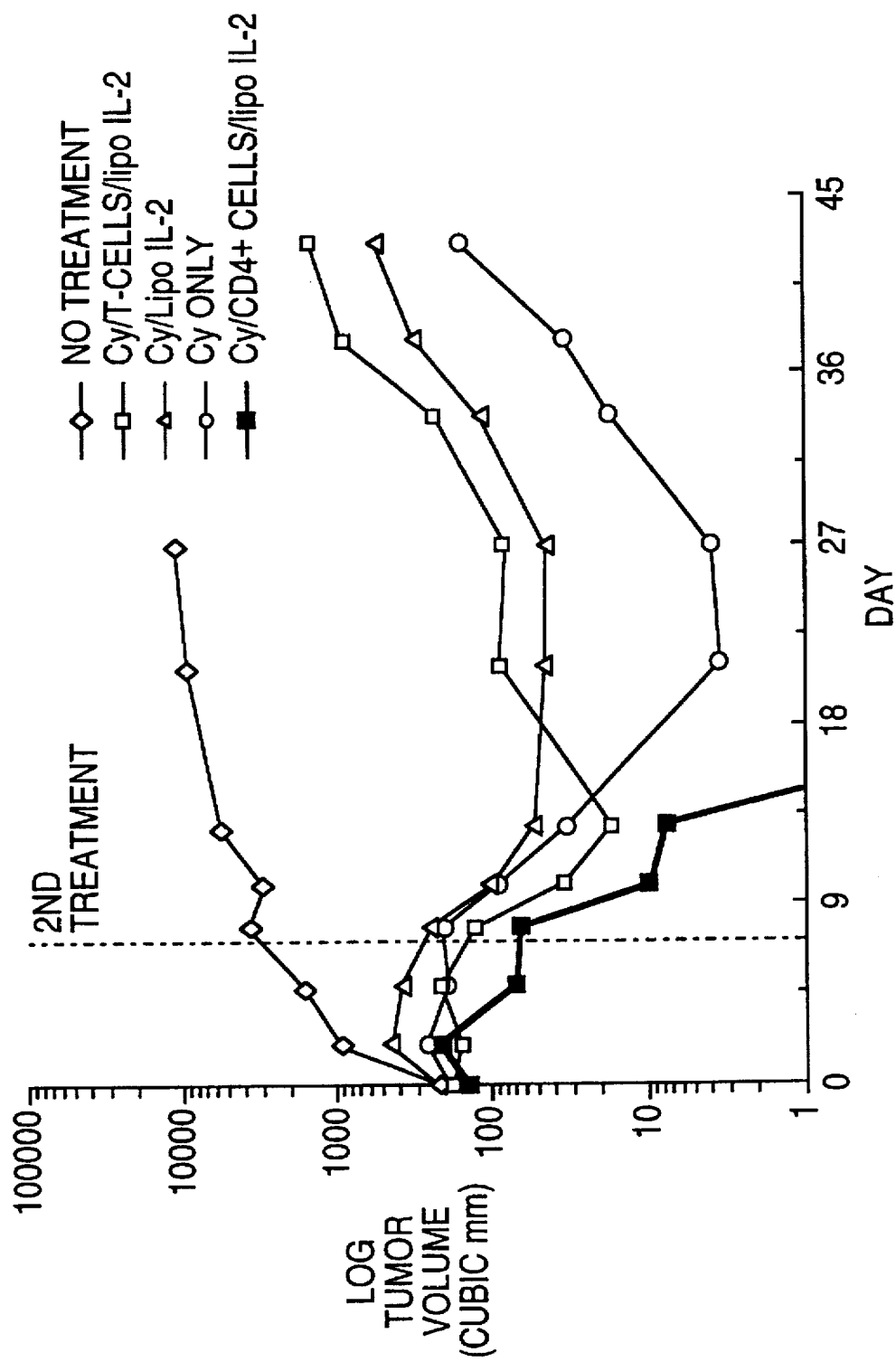
FIG. 7 illustrates the ability of stimulated depleted $CD4^+$ cells to substantially eradicate a tumor in vivo when stimulated in the presence of anti-CD3 and a relatively minor amount of IL-2, and then administered to a mammal initially and then administered a second time.

One group of the mice which had tumors ringing from 140 to about 220 mm$^3$ received no treatment (represented by the empty diamond in FIG. 7), another group received injections of CYTOXAN only (represented by the empty circle in FIG. 7). A third group of mice received CYTOXAN and liposomal IL-2 (represented by the empty triangle in FIG. 7), while a fourth group of mice received an intravenous injection of cultured undepleted cells and CYTOXAN, and an intraperitoneal injection of IL-2 (represented by the empty box in FIG. 7). The fifth group of mice represented the inventive group, and received an intravenous injection of CYTOXAN prior to an intravenous injection of stimulated CD4+ cell subpopulation and an intraperitoneal injection of liposomal IL-2 (represented by the black box in FIG. 7).

As can be seen from. FIG. 7, the stimulated cell subpopulation cultured in the presence of an antibody to a lymphocyte surface receptor and a relatively minor mount of IL-2 for less than 48 hours, showed an enhanced anti-tumor immunotherapeutic activity when compared to similarly treated unseparated cells. Indeed, administering the CD4+ cell subpopulations to the mice initially and at day 7 together with CYTOXAN and liposomal IL-2 resulted in substantial eradication of the MCA-38 tumor after about 14 days. One skilled in the art would expect that an analogous human stimulated immune cell subset cultured in the presence of an antibody to a lymphocyte surface receptor and a relatively minor mount of IL-2 for less than 48 hours would provide a similar result in humans.

EXAMPLE 8

Long-Term Immunity Of Mammals Treated With

Cell Subpopulations Having Enhanced Immunotherapeutic

Activity In Vivo

Eight C57BL/6 mice that received the initial and second administration of stimulated CD4+, CYTOXAN and liposomal IL-2 were rechallenged with the same MCA-38 tumor (1×10$^6$ cells administered subcutaneously) in the right hind flank 82 days after initial treatment. Control C57BL/6 mice that received no treatment also were rechallenged with the same MCA-38 tumor. All of the control mice died of tumor whereas the eight treated mice all survived and had no tumor after 45 days.

Four of these eight mice then were challenged again with a different rumor (B16 melanoma 1×10$^6$ cells administered subcutaneously) and died within two weeks of tumor. The four remaining treated mice as well as a group of control mice were again challenged with the same MCA-38 tumor after 180 days from the initial treatment. Again, all of the control mice died from tumor, but the treated mice did not develop any tumor after 30 days.

This example clearly illustrates the long-term immunity of stimulated CD4+ cell subpopulations when administered with CYTOXAN intravenously together with an intraperitoneal injection of liposomal IL-2. Hence, mice that were administered the aforementioned stimulated cells developed an immunity to tumors and substantially eradicated the tumors even after being challenged with the tumors three times over a period of 180 days.

EXAMPLE 9

Transferable Immunity Of Mammals Treated With

Cell Subpopulations Having Enhanced Immunotherapeutic

Activity In Vivo

The four remaining C57BL/6 mice that survived the tumor rechallenges described in Example 8 above were sacrificed. Splenocytes were extracted from the sacrificed mice Using the conventional techniques outlined above. Approximately 5×10$^7$ splenocyte cells from the treated mice were injected into naive C57BL/6 mice. These treated mice as well as control mice then were challenged with MCA-38 tumor (1×10$^5$ cells subcutaneously).

All of the control mice died of tumor within 30 days whereas the mice treated in accordance with the present invention exhibited no evidence of rumor. These results indicate the transferable immunity effect in mammals of the stimulated CD4+ cell subpopulations cultured and administered in accordance with the present invention.

EXAMPLE 10

Increasing The Number Of Bone Marrow Cells

Bone marrow cells were obtained from a donor by conventional methods and separated over ficoll-hypaque and frozen. Cells also were obtained from the same human donor (P. L.; M42389) by leukaphoresis, separated over ficoll-hypaque and frozen. These cells were subsequently thawed and separated using human T cell and human CD4 subset columns (R & D Systems Human Select) in accordance with the kit instructions. The separated CD4+ cell subsets then were activated with 10 ng/ml human anti-CD3 and placed into culture with 100 units/ml IL-2 for 24 hours to produce stimulated CD4+ cell subsets.

These cell subsets then were placed into colony assays, according to conventional procedures, in several combinations with fresh, ficoll-separated bone marrow cells (P. L.; M42961) and incubated for 14 days at 37° C. Bone marrow (BM) and stimulated CD4+ cells were plated at a 1:1 ratio (10$^5$:10$^5$; BM:CD4+) when used in combination or plated at a concentration of 10$^5$ cells/plate when plated alone. Various combinations of BM and CD4⁺ cells and conditioned media (CM) were incubated together with cytokines such as IL-2, GM-CSF, IL-3, KL, Epo for 14 days at 37° C. Colonies were scored after 14 days of incubation where 50 or more cells constitute a colony. Three trials were run for each combination. The results are shown in Table 2 below.

TABLE 2

| Combination | Colony Forming Units Produced | | |
|---|---|---|---|
| BM alone | 0 | 0 | 2 |
| BM + IL-2 | 1 | 2 | 2 |
| CD4⁺ + IL-2 | 1 | 0 | 1 |
| BM + CD4⁺ + IL-2 | 15 | 6 | 7 |
| BM + CM + Epo + IL-2 | 14 | 16 | 21 |
| BM + IL-3 + GM-CSF + KL + IL-2 | 88 | 75 | 99 |

The results illustrated above indicate that stimulated CD4⁺ cells produce various cytokines which when combined with bone marrow cells are capable of stimulating growth of bone marrow cells. Even without the addition of cytokines, stimulated CD4⁺ cells, when contacted with bone marrow cells and IL-2 stimulated the production of significantly more boric marrow cells than bone marrow or stimulated CD4⁺ cells alone. The addition of KL to bone marrow cells provided a synergistic proliferative effect since, it is believed, the KL provides for stimulation of early growth and progression of progenitor cells of bone marrow.

EXAMPLE 11

Increasing The Number Of Bone Marrow Cells After 72 Hours Of Activation

The same procedures were carried out as above, only the separated CD4⁺ were activated for 24 hours and for 72 hours to produce two separate groups of stimulated CD4⁺ cell subsets. These two groups then were incubated with bone marrow and various combinations of exogenous cytokines for 14 days at 37° C. In addition, the Kit Ligand cytokine was added to the BM+CD4⁺+Il-2 combination used in Example 10. The results are shown in Table 3 below.

TABLE 3

| Combination | Colony Forming Units (24 hours Activation) | | | Colony Forming Units (72 hours Activation) | | |
|---|---|---|---|---|---|---|
| BM alone | 2 | 3 | 0 | 2 | 2 | 0 |
| BM + IL-2 | 1 | 2 | 0 | — | 0 | 2 |
| CD4⁺ + IL-2 | 0 | 0 | 0 | 6 | 2 | 6 |
| BM + CD4⁺ + IL-2 | 9 | 5 | 5 | 19 | 22 | 26 |
| BM + CM + Epo + IL-2 | 44 | 21 | 55 | 22 | 27 | 29 |
| BM + IL-3 + GM-CSF + KL + Epo + IL-2 | 84 | 79 | 76 | 63 | 48 | 63 |
| BM + CD4⁺ + KL + IL-2 | 17 | 28 | 24 | 73 | 77 | 72 |

The results illustrated in Table 3 above indicate that an additional three days of culturing of the stimulated CD4⁺ cells stimulated bone marrow cell production even further without the addition of exogenous cytokines. The use of CD4⁺ cells, IL-2 and KL, however, provided a significantly increased stimulation of bone marrow cell production. The additional activation period of 72 hours as opposed to 24 hours indicates that the amount of cytokine production by the stimulated cells was further increased thereby increasing the total number of bone marrow cells produced.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. A method of treating a mammal having tumors, comprising optionally administering to said mammal an immunosuppressant, and then administering to said mammal (1) either a stimulated CD8⁺—depleted T cell subpopulation or a stimulated CD4⁺ T cell subsist, and (2) liposomal IL-2; wherein said stimulated CD8⁺—depleted T cell subpopulation is produced by:

(i) separating CD8⁺ lymphocytes from a T cell population to form a CD8⁺—depleted T cell subpopulation;

(ii) culturing said CD8⁺—depleted T cell subpopulation in the presence of an anti-CD3 monoclonal antibody, optionally in the presence of IL-2, during a first 48 hour time period of culture to provide a stimulated CD8⁺—depleted immune cell subpopulation, wherein said IL-2 is present in an amount sufficient to sustain said immune cell subpopulation at about its initial cell density; and (iii) optionally subculturing the stimulated CD8⁺—depleted T cell subpopulation in a second medium comprising IL-2, wherein said IL-2 is present in an amount sufficient to sustain said stimulated CD8⁺—depleted immune cell subpopulation at about its initial cell density, wherein the stimulated CD8⁺—depleted T cell subpopulation exhibits increased antitumor activity when stimulated with IL-2, due primarily to the enhanced responsiveness to IL-2 of the stimulated CD8⁺—depleted T cell subpopulation, when compared to a similarly treated undepleted T cell population, and wherein said stimulated CD4⁺ T cell subset is produced by:

(i) separating and selecting CD4⁺ lymphocytes from a T cell population to form a CD4⁺—depleted T cell population and a CD4⁺ T cell subset;

(ii) culturing the CD4⁺ T cell subset in the presence of an anti-CD3 monoclonal antibody, optionally in the presence of IL-2, during a first 48 hour time period of culture to provide a stimulated CD4⁺ immune cell subset, wherein said IL-2 is present in an amount sufficient to sustain said CD4⁺ immune cell subset at about its initial cell density; and (iii) optionally subculturing the stimulated CD4⁺ T cell subset in a second medium comprising IL-2, wherein said IL-2 is present in an amount sufficient to sustain said CD4⁺ immune cell subset at about its initial cell density, wherein the stimulated CD4⁺ T cell subset exhibits increased antitumor activity when stimulated with IL-2, due primarily to the enhanced responsiveness to IL-2 of the stimulated CD4⁺ T cell subset when compared to a similarly treated undepleted cell population.

2. The method of claim 1, wherein said immuosuppressant is cyclophosphamide.

3. The method of claim 1, wherein said IL-2 is present at a concentration of less than about 100 units/ml.

4. A method of treating a mammal having tumors, comprising:

(a) administering to said mammal cyclophosphamide, and then;

(b) administering to said mammal (1) a stimulated CD4⁺ cell subpopulation prepared by culturing a removed CD4+ cell subpopulation, which has been separated from a T cell population, in the presence of an anti-CD3 monoclonal antibody and about 100 units/ml IL-2, during a first 48 hour time period of culture to provide a stimulated CD4+ cell subpopulation, wherein the stimulated CD4+ cell subpopulation exhibits increased antitumor activity due primarily to the enhanced responsiveness to IL-2 of the stimulated CD4+ subpopulation, when compared to a similarly treated undepleted T cell population, and (2) liposomal IL-2.

* * * * *